United States Patent
Harper

(10) Patent No.: US 10,772,663 B2
(45) Date of Patent: *Sep. 15, 2020

(54) INSTRUMENTS FOR USE DURING SPINE SURGERY

(71) Applicant: GLOBUS MEDICAL, INC., Audubon, PA (US)

(72) Inventor: Michael Harper, Pottstown, PA (US)

(73) Assignee: Globus Medical, Inc., Audubon, PA (US)

( * ) Notice: Subject to any disclaimer, the term of this patent is extended or adjusted under 35 U.S.C. 154(b) by 65 days.

This patent is subject to a terminal disclaimer.

(21) Appl. No.: 16/153,946

(22) Filed: Oct. 8, 2018

(65) Prior Publication Data

US 2019/0090916 A1 Mar. 28, 2019

Related U.S. Application Data

(63) Continuation of application No. 15/358,268, filed on Nov. 22, 2016, now Pat. No. 10,123,826, which is a continuation of application No. 14/213,055, filed on Mar. 14, 2014, now Pat. No. 9,532,814.

(60) Provisional application No. 61/783,652, filed on Mar. 14, 2013.

(51) Int. Cl.
| | |
|---|---|
| *A61B 17/70* | (2006.01) |
| *A61B 17/56* | (2006.01) |
| *B25B 13/46* | (2006.01) |
| *A61B 17/88* | (2006.01) |
| *A61B 17/00* | (2006.01) |

(52) U.S. Cl.
CPC .......... *A61B 17/7082* (2013.01); *A61B 17/56* (2013.01); *A61B 17/7074* (2013.01); *A61B 17/7076* (2013.01); *A61B 17/7083* (2013.01); *A61B 17/7085* (2013.01); *A61B 17/7086* (2013.01); *A61B 17/7088* (2013.01); *A61B 17/7091* (2013.01); *A61B 17/8872* (2013.01); *A61B 17/8875* (2013.01); *A61B 17/8886* (2013.01); *A61B 17/8888* (2013.01); *A61B 17/8891* (2013.01); *B25B 13/46* (2013.01); *B25B 13/466* (2013.01); *B25B 13/468* (2013.01); *A61B 2017/00407* (2013.01); *A61B 2017/564* (2013.01)

(58) Field of Classification Search
CPC .............. A61B 17/56; A61B 2017/564; A61B 17/7074; A61B 17/7076; A61B 17/7082; A61B 17/7083; A61B 17/7085; A61B 17/7086; A61B 17/7088; A61B 17/7091; A61B 17/88; A61B 17/8872; A61B 17/8875; A61B 17/8886; A61B 17/8888; A61B 17/8891; B25B 13/46; B25B 13/466; B25B 13/468

See application file for complete search history.

(56) References Cited

U.S. PATENT DOCUMENTS

| | | | |
|---|---|---|---|
| 9,532,814 B2 * | 1/2017 | Harper | A61B 17/7086 |
| 2011/0313463 A1 * | 12/2011 | McLean | A61B 17/708 606/279 |

* cited by examiner

*Primary Examiner* — Larry E Waggle, Jr.

(57) ABSTRACT

Surgical instruments and devices including drivers, inserters, and reducers. The driver includes a ratcheting mechanism configured to provide uni-directional motion when engaged. The inserter includes a rack, pinion, and cam system designed to secure an implant and release an implant in-situ. The reducer includes a geared system for persuading together surgical components and aligning misaligned vertebrae.

15 Claims, 22 Drawing Sheets

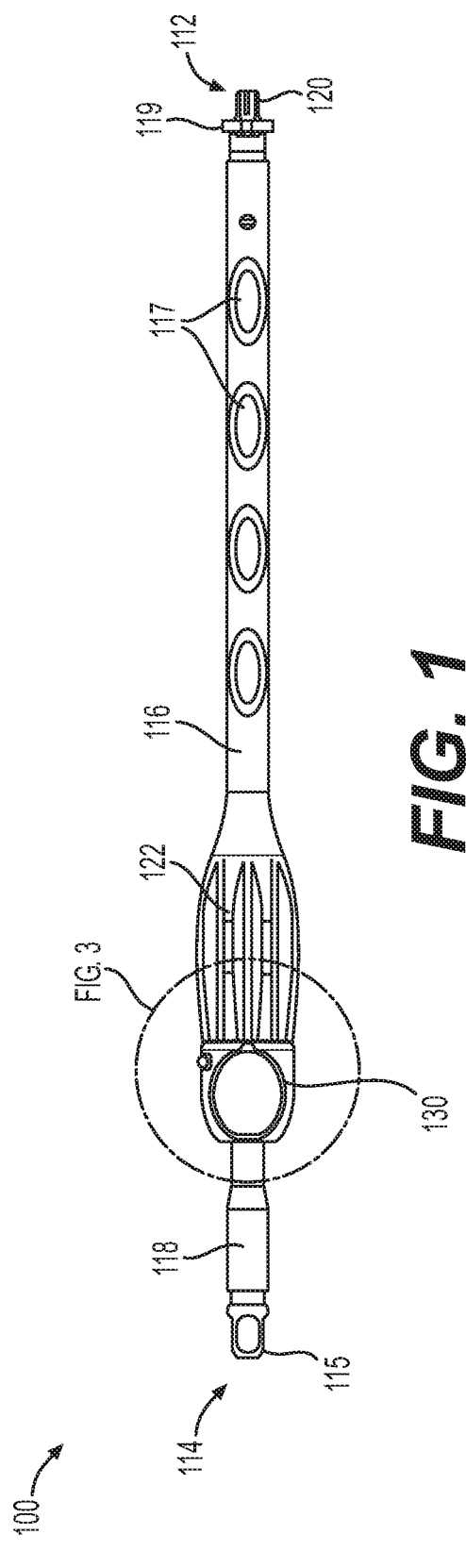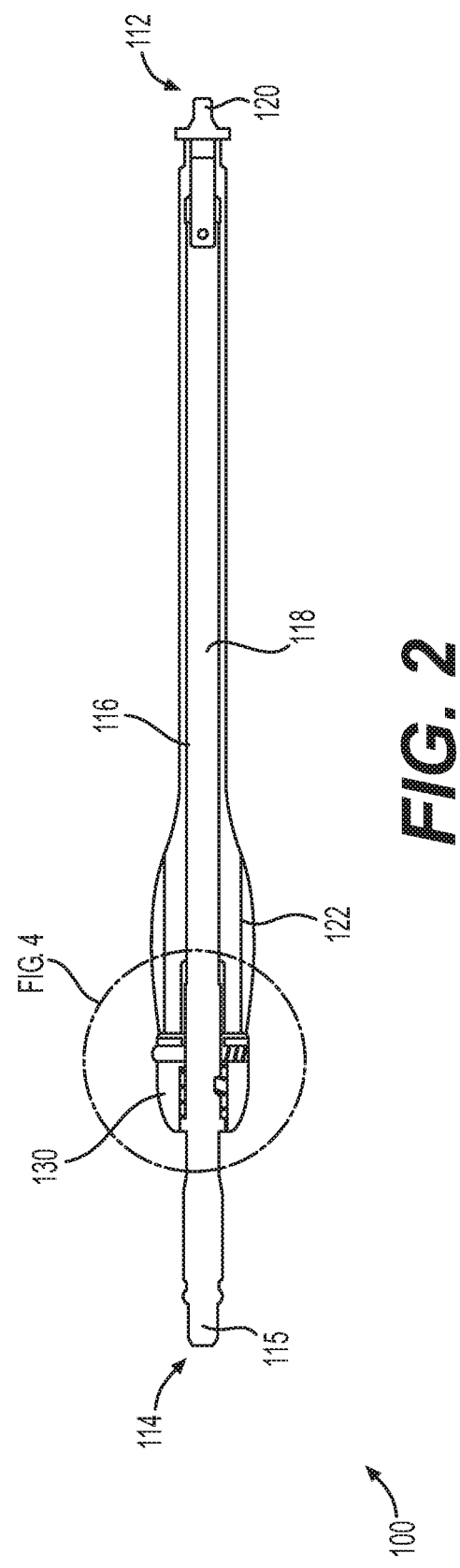

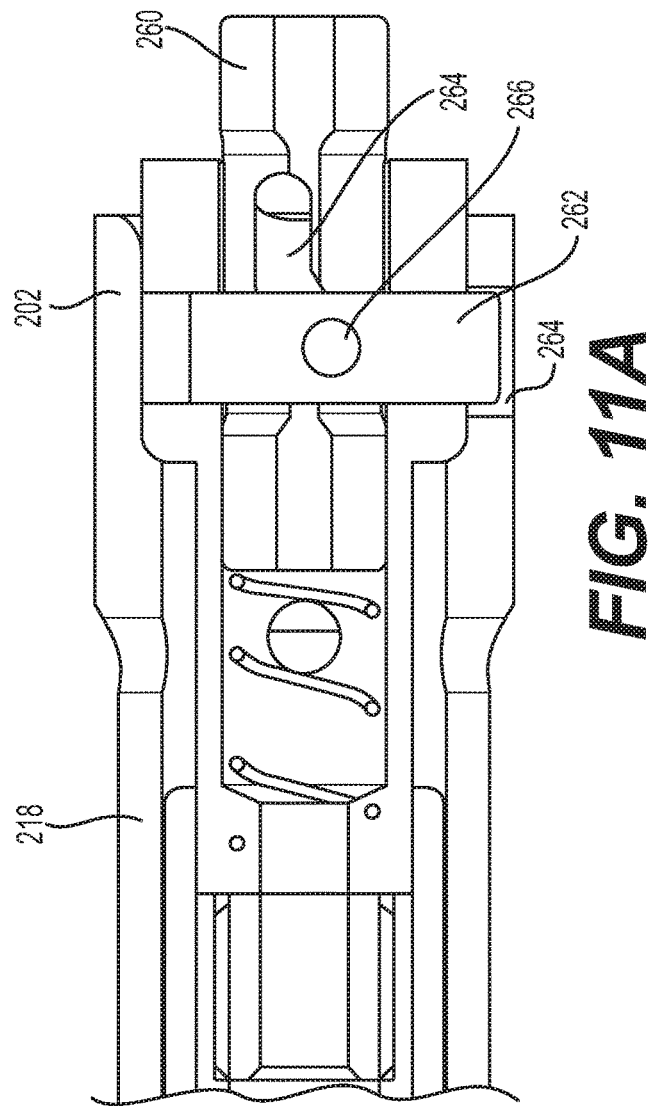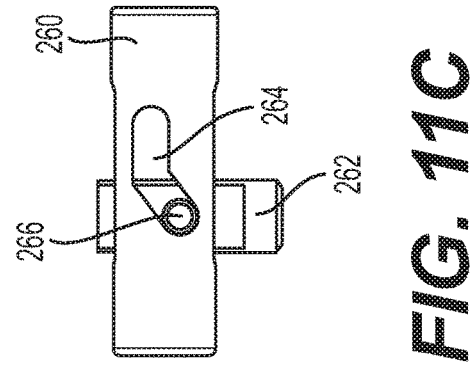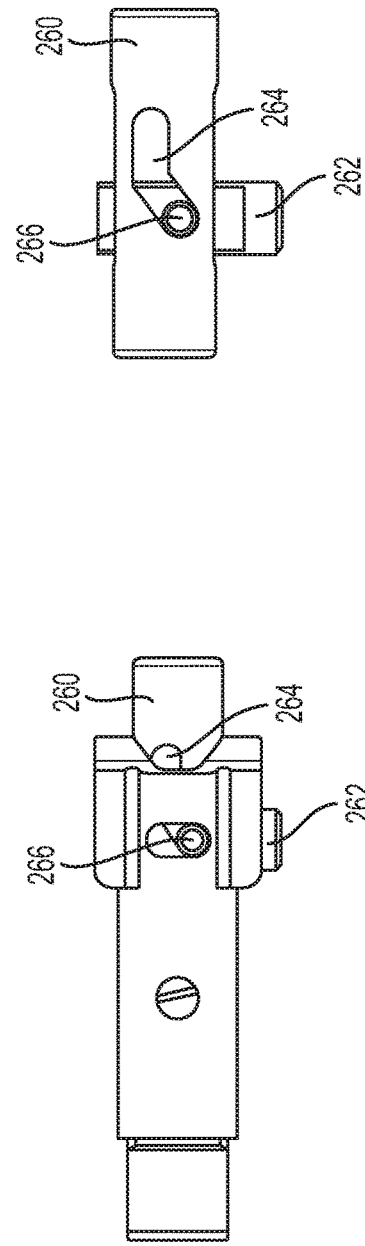
*FIG. 11A*
*FIG. 11B*
*FIG. 11C*

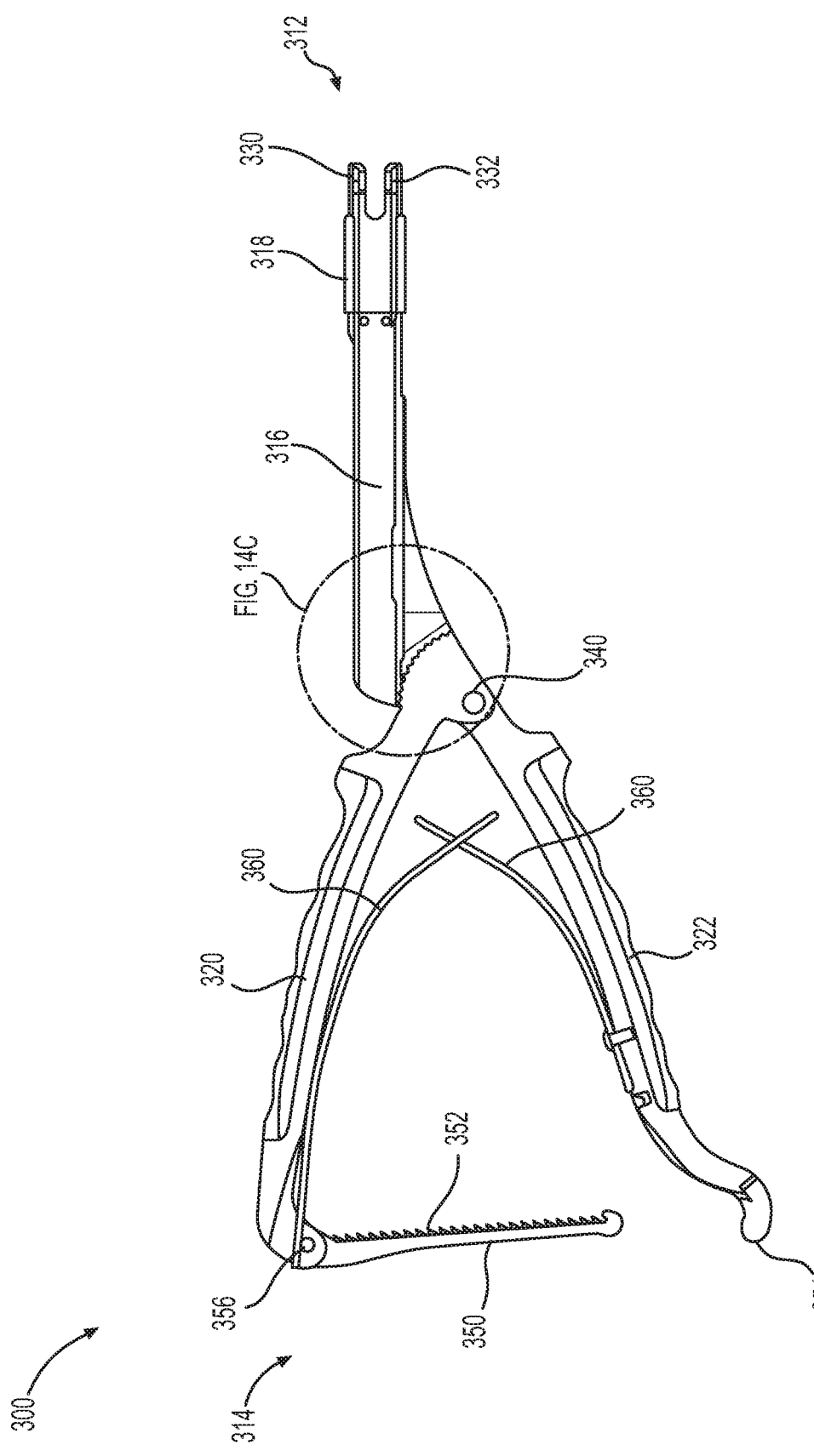

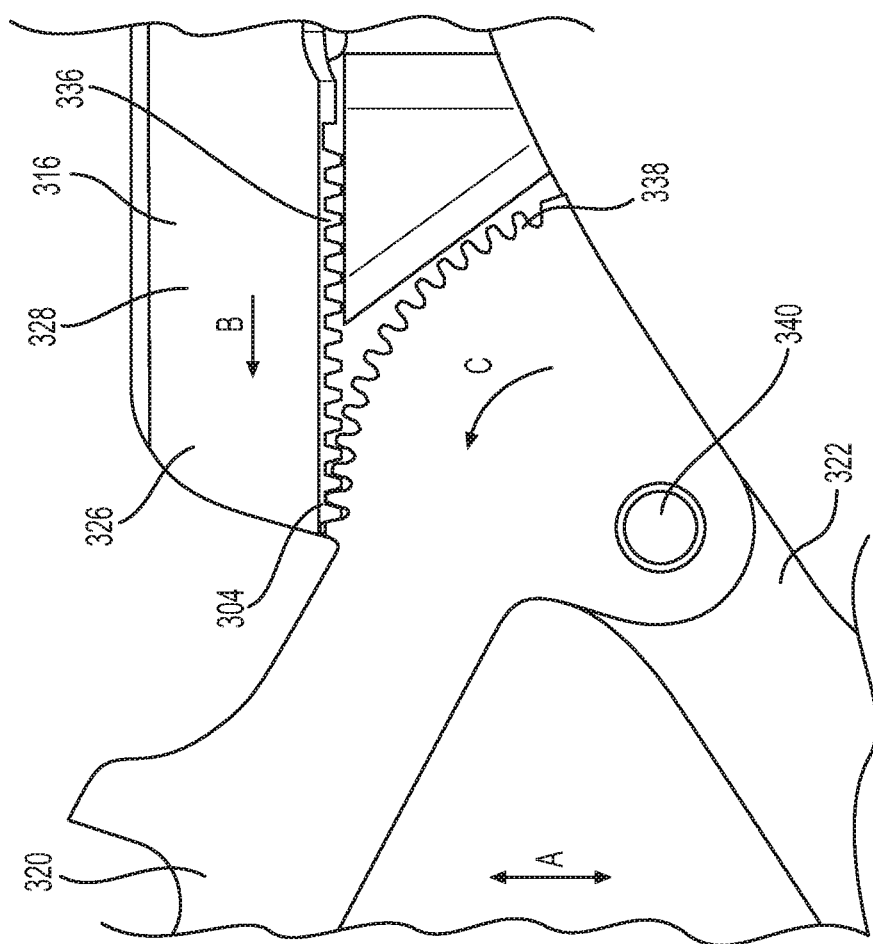

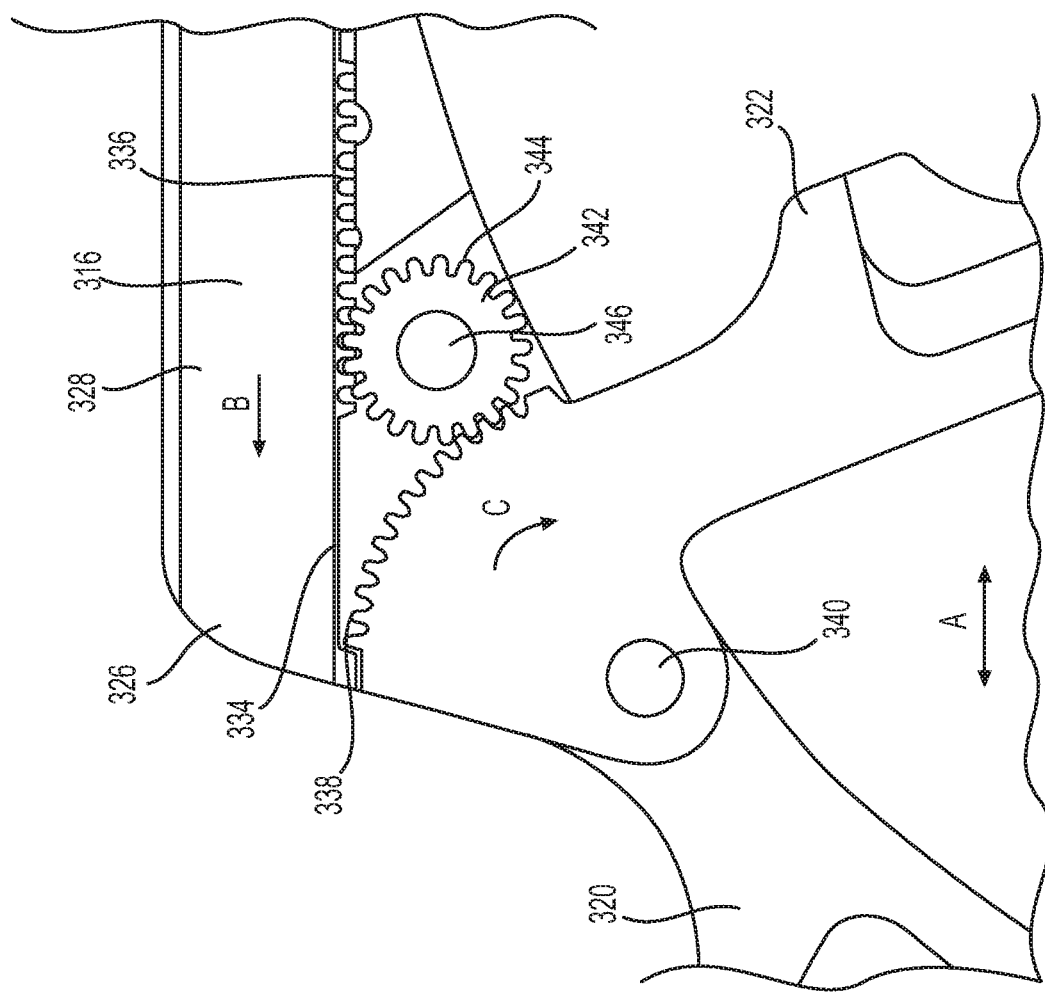

INSTRUMENTS FOR USE DURING SPINE SURGERY

CROSS-REFERENCE TO RELATED APPLICATIONS

This application is a continuation of U.S. patent application Ser. No. 15/358,268 filed on Oct. 11, 2018 which is a continuation of U.S. patent application Ser. No. 14/213,055, filed Mar. 14, 2014, which claims priority to U.S. provisional application No. 61/783,652 filed Mar. 14, 2013. The entire contents of these documents are incorporated herein by reference in their entireties for all purposes.

FIELD OF THE INVENTION

The present disclosure generally relates to devices used in surgery. More particularly, the surgical devices include instruments and tools for spinal surgery and fixation procedures.

BACKGROUND OF THE INVENTION

Many types of spinal irregularities can cause pain, limit range of motion, or injure the nervous system within the spinal column. These irregularities can result from, without limitation, trauma, tumor, disc degeneration, and disease. Often, these irregularities are treated by immobilizing a portion of the spine. This treatment typically involves affixing a plurality of fixation devices to one or more vertebrae and connecting the devices to an elongate rod that generally extends in the direction of the axis of the spine.

Treatment for these spinal irregularities often involves using a system of fixation devices to attain stability between spinal segments. Instability in the spine can create stress and strain on neurological elements, such as the spinal cord and nerve roots. In order to correct this, implants of certain stiffness may be implanted to restore the correct alignment and portion of the vertebral bodies. In many cases, a fixation device along with a vertical solid member can help restore spinal elements to a pain free situation, or at least may help reduce pain or prevent further injury to the spine.

Typically, fixation devices may include a bone fastener (e.g., bone screw, hook, etc.) for coupling the fixation device to vertebra. Fixation devices further may include a coupling element (e.g., a tulip element) for coupling the bone fastener to the vertical solid member (e.g., elongate rod). Clamp and/or wedge elements may be used to secure the bone fastener in the coupling element. A locking cap may be used to secure the rod in the coupling element. In order for the elements of the fixation device to be secured, the rod may need to be seated firmly in the coupling element. A variety of methods and instruments may be used to maximize engagement between the rod and the coupling element and attachment of the fixation devices.

Traditionally, these types of spinal devices were installed via open-back surgery. This type of procedure tended to cause extensive trauma to the patient, resulting in long and painful recovery times. In recent years, a shift has been made toward minimally invasive surgery (MIS) techniques. In minimally invasive surgery, the surgeon makes small incisions and uses special tools to insert devices, observe progress of the operation, and perform other activities in the surgical site. Minimally invasive surgical techniques frequently result in much less injury to the patient and improved healing and recovery times. In a minimally invasive procedure, however, it may be more difficult for the physician to insert and secure the fixation devices, maneuver the rod, or the like. There is a need for improved tools and instrumentation, for example, suitable for use in minimally invasive procedures.

SUMMARY OF THE INVENTION

To meet these and other needs, a number of surgical instruments and devices are provided. In particular, a surgical instrument having a ratcheting mechanism for driving a fastening element (e.g., pedicle screws or other bony anchors) includes a secure lock with the added advantage of in-situ uni-directional tightening. A surgical instrument may include a number of mechanisms to increase the functionality and safety for inserting a surgical device, such as an implant. A surgical instrument also includes one or more reducers suitable for persuading together, for example, a rod and a seat recess of an orthopedic device or coupling element, such as a pedicle screw assembly, in order to align misaligned vertebrae.

According to one embodiment, a surgical instrument for driving a fastening element (e.g., a driver) includes a ratcheting mechanism. The surgical driver includes an outer housing and a shaft contained within the outer housing. The shaft has a first end configured for engaging a fastener and a second end configured for providing a rotational force. The surgical driver includes a locking element connected to the shaft and having an engaging face with a first plurality of ratchet teeth. The locking element is configured to move longitudinally along the shaft. The outer housing includes a handle having a contacting face with a second plurality of ratchet teeth sized and dimensioned to correspond with the first plurality of ratchet teeth of the locking element.

The locking element also includes a locking button disposed thereon and configured to engage the shaft such that when the locking button is depressed, the first plurality of ratchet teeth on the engaging face contact and mate with the second plurality of ratchet teeth on the contacting face, and the ratcheting mechanism is engaged. The locking element may include a spring which surrounds the shaft and forces the ratcheting mechanism to remain engaged. The shaft may include a notch such that when the locking button is engaged in the notch, the first plurality of ratchet teeth on the engaging face teeth are separated a distance from the second plurality of ratchet teeth on the contacting face, and the ratcheting mechanism is not engaged.

According to another embodiment, a surgical instrument for inserting a surgical device includes a body having an outer housing and a handle. The outer housing has a longitudinal body with a channel extending therethrough and a distal tip configured to engage the surgical device. A shaft including a release shaft has a distal end configured to contact the surgical device and a second opposite end. The shaft is housed within the channel of the outer housing, and the shaft includes a rack having a longitudinal body with a plurality of teeth. A pinion having a wheel-like body with a plurality of teeth radially extending therefrom is configured to mate with the plurality of teeth of the rack. A cam having a generally circular body with at least one projection is rotatably attached to the pinion and the body. A trigger is coupled to the handle and includes a linkage connecting the trigger to the second end of the shaft. When the trigger is initially depressed, the linkage moves the shaft and secures the surgical device to the distal tip. When the trigger is fully depressed, the linkage moves the rack and rotates the pinion and the cam, which thereby moves the release shaft and releases the surgical device.

According to another embodiment, a method of using an inserter instrument includes the steps of: (a) unlocking the instrument by depressing the safety lock; (b) connecting the surgical device to the distal tip of the instrument by apply an axial force; (c) locking the surgical device to the instrument by slightly depressing the trigger; (d) performing the surgical procedure; and (e) releasing the surgical device from the instrument by fully depressing the trigger.

According to yet another embodiment, a surgical instrument for reducing a bone fastener toward a rod includes a reducing member, an outer longitudinal member, and a handle. The reducing member extends between a proximal end and a distal end. A distal portion of the reducing member is adapted to receive a portion of the bone fastener, and a proximal portion of the reducing member has a first plurality of gear teeth. The outer longitudinal member is sized and shaped to receive the reducing member. The handle includes at least one trigger element. The trigger element has a second plurality of gear teeth configured to cause translation of the reducing member with respect to the outer longitudinal member when a force is applied to the handle.

The gear teeth of the trigger element may be directly or indirectly in contact with the gear teeth of the reducing member. In one embodiment, the second plurality of gear teeth on the trigger element are configured to directly engage and mate with the first plurality of gear teeth on the reducing member to cause the reducing member to move proximally. In another embodiment, a pinion gear is sandwiched between the gear teeth of the reducing member and the gear teeth of the trigger element. In particular, the second plurality of gear teeth on the trigger element are configured to contact and rotate the pinion gear, and the pinion gear is configured to contact at least a portion of the first plurality of gear teeth on the reducing member to cause the reducing member to move proximally. The surgical instruments may include other features, such as a ratcheting mechanism on an end of the trigger element to uni-directionally ratchet the reducing member.

BRIEF DESCRIPTION OF DRAWING

The invention is best understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following figures:

FIG. 1 depicts a side view of an instrument for driving a fastening element according to one embodiment;

FIG. 2 shows a cross-sectional view of the driving instrument of FIG. 2;

FIGS. 11A-11C show components of a locking mechanism (when locked) used at the distal tip of the retention shaft in the inserter instrument depicted in FIG. 6A;

FIGS. 14A-C depicts one embodiment of an instrument with a geared reducer;

FIGS. 15A-C provide an alternative embodiment of an instrument with a geared reducer.

DETAILED DESCRIPTION OF THE INVENTION

Figure 3:
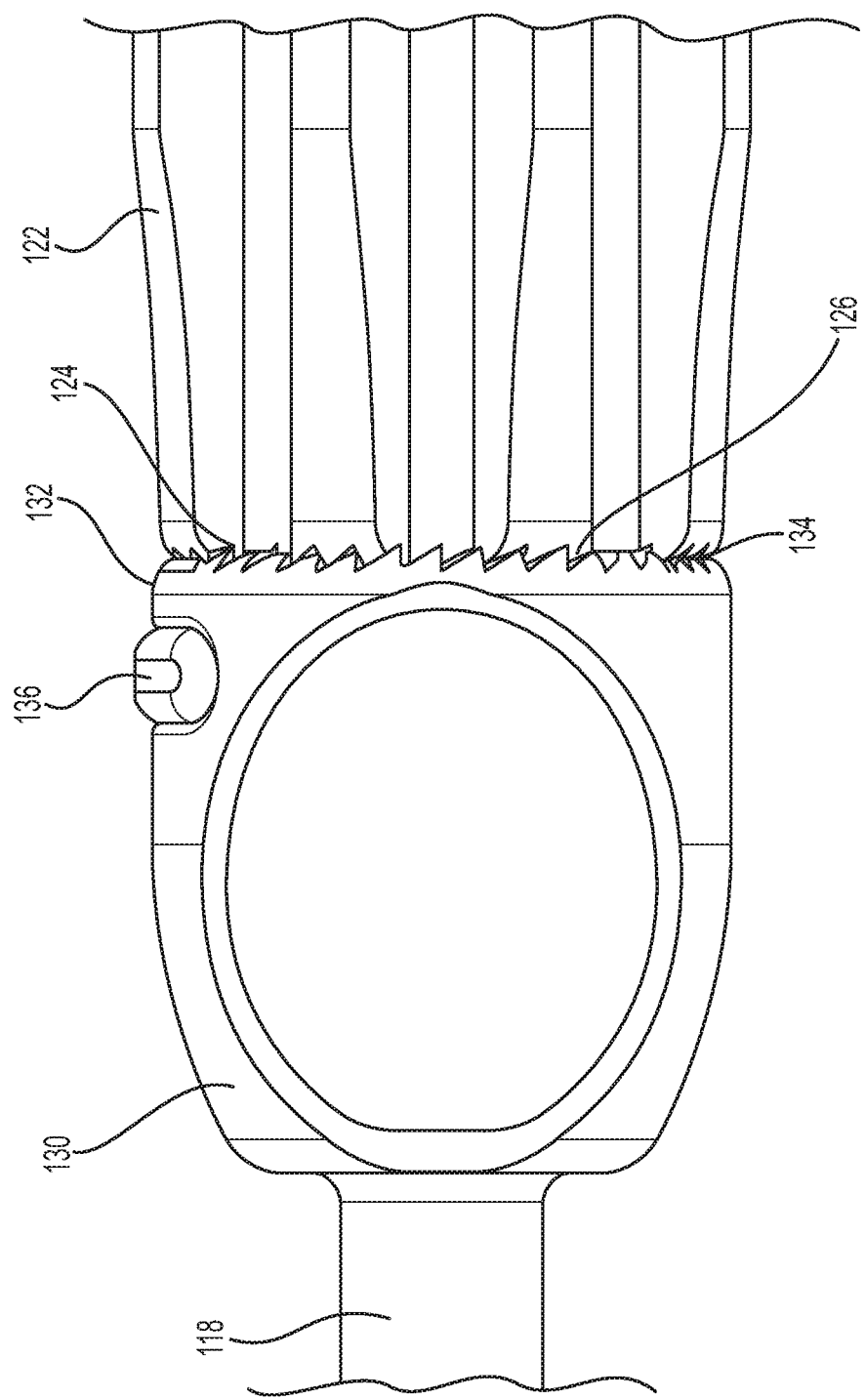
FIG. 3 shows a close-up view of a portion of the driving instrument shown in FIG. 1.

Embodiments of the disclosure are generally directed to surgical instruments and devices including drivers, inserters, reducers, and the like. The surgical devices may be adapted to permit insertion through a minimally invasive procedure or micro-incision. The surgical devices are also especially suitable for spinal surgeries and procedures. Examples of surgical procedures suitable for employing the surgical devices described herein include, but are not limited to, insertion and securement of interbody fusion devices, bone anchors, fixation devices, including rods, plates and cables, fasteners (such as screws and caps), artificial disks, hip stems, artificial ligaments, trochars for gastro-intestinal work, or any procedure operating on a patient.

As used herein and in the claims, the terms "comprising" and "including" are inclusive or open-ended and do not exclude additional unrecited elements, compositional components, or method steps. Accordingly, the terms "comprising" and "including" encompass the more restrictive terms "consisting essentially of" and "consisting of." It is also noted that, as used in this disclosure and the appended claims, the singular forms "a," "an" and "the" include plural referents unless the context clearly dictates otherwise. Furthermore, the words "proximal" and "distal" refer to directions closer to and further away from a reference point, respectively. For example, an operator (e.g., surgeon, physician, nurse, technician, medical professional, etc.) may insert the instrument into the patient with the tip-end (e.g., the distal end) of the device toward a patient's body.

According to one embodiment, FIGS. 1-5 depict alternate views of a surgical instrument 100 (also called a driver 100) suitable for driving or securing a fastening element, such as a screw, cap, or the like. The surgical instrument 100 may be in the form of a screwdriver for the insertion of pedicle screws or other bony anchors. The instrument 100 may be similar to competitive drivers in function, but includes at least a novel locking mechanism. Unlike traditional screwdrivers which may become loose during anchor insertion, the surgical instrument 100 allows for a simple lock and unlock mechanism while still allowing the surgeon to further tighten the driver without additional steps.

The surgical instrument 100 includes an outer housing 116. The outer housing 116 has a body which is generally hollow and defines a channel extending longitudinally through it and is sized and shaped to receive a shaft 118 therein. The outer housing 116 may include one or more windows 117 suitable for viewing the shaft 118. The shaft 118 has a first end (e.g., distal end 112) configured for engaging a fastener and a second end (e.g., proximal end 114) configured for providing a rotational force (e.g., a torque). The shaft 118 may include one or more threaded portions 119, for example, proximate to the distal end 112. The threaded portion 119 may be configured to engage a portion of the fastener or an additional threaded component, such as an extension from the fastening element (e.g., a tulip or yoke).

As is evident in FIGS. 1 and 2, the distal end 112 includes a tip 120 suitable for engaging a fastener. The tip 120 may include any typical screwdriver bit, such as a Phillips screwdriver tip, a slot-head tip, a Robertson-head tip, an Allen-wrench tip, a hexagonal-head tip, a TORX® head tip, a key, or the like. The tip 120 may have any suitable cross-sectional configuration designed to engage with a fastening element. Suitable fastening elements include screws (e.g., bone screws, pedicle screws, or other bony anchors), caps, bolts, nuts, tulips, yokes, locking elements (e.g., for anti-backout prevention), etc. The fastening elements may include those exemplified, for example, in U.S. Publication No. 2013/0018428, which is hereby incorporated by reference in its entirety for all purposes. The shaft 118 may have an instrument interface 115 shaped to receive torque from a driver (not shown). The instrument interface 115 may also have any suitable shape, such as a polygonal cross sectional shape, hexagonal shape, or the like, as needed to apply an appropriate torque or rotational force to the shaft 118.

Figure 4:
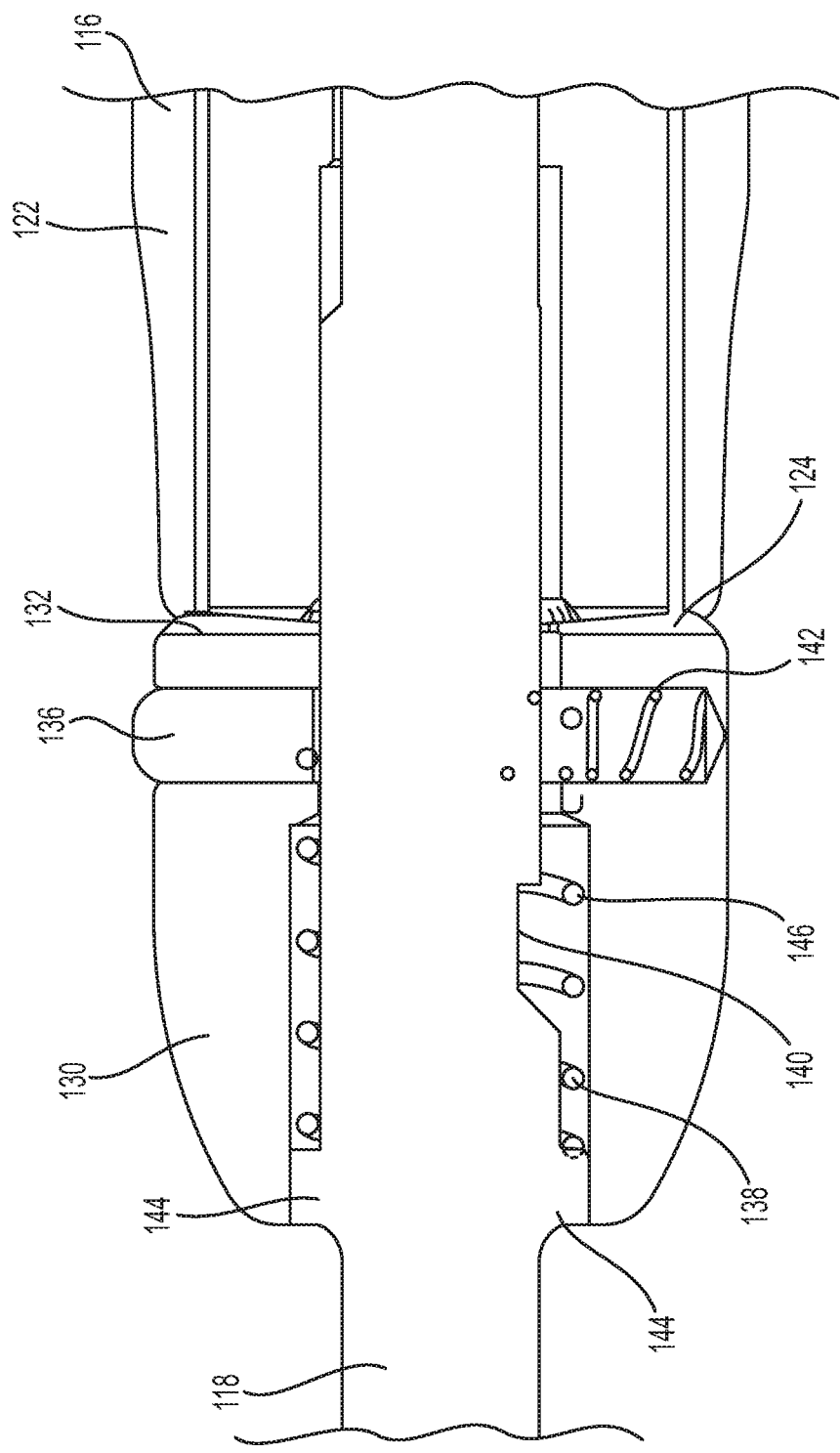
FIG. 4 shows a close-up view of a portion of the driving instrument shown in FIG. 2 when the button is not engaged in the shaft.
Figure 5:
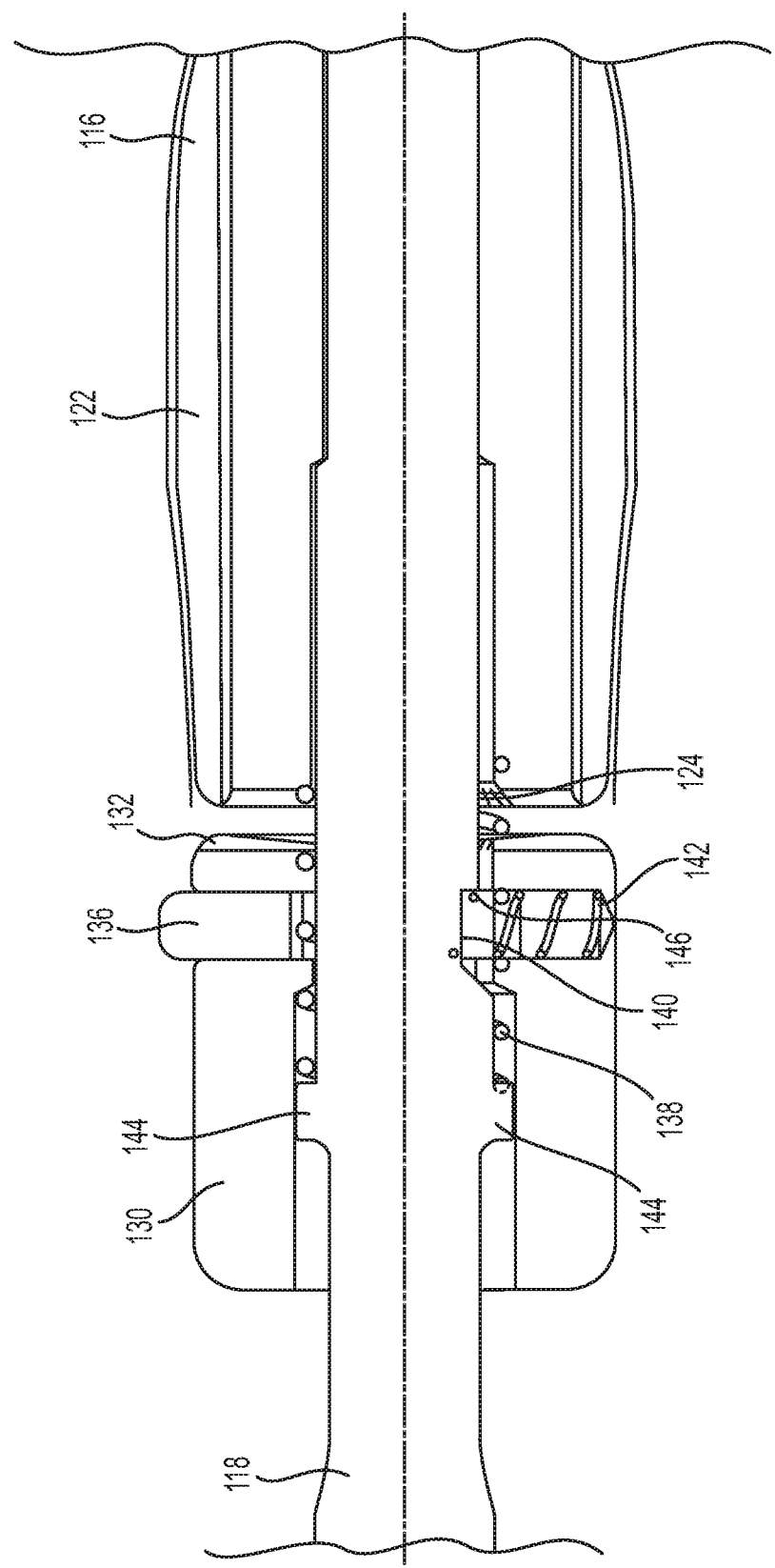
FIG. 5 depicts a close-up view of the portion of the driving instrument shown in FIG. 4 when the button is engaged with the shaft.

As shown in FIG. 3, the surgical instrument 100 includes a locking element 130. The locking element 130 may include a generally cylindrical-shaped body, which is generally hollow, and defines a channel extending longitudinally therethrough. The locking element 130 is sized and shaped to receive the shaft 118 and surrounds the shaft 118. The locking element 130 may be connected to the shaft 118, for example, such that it is able to rotate about the shaft 118 and/or move longitudinally along the length of the shaft 118. As shown in FIG. 4, the locking element 130 may also house a spring 138, which is sleeved on the shaft 118. The spring 138 pushes against one or more tabs 144 (e.g., a generally cylindrical tab 144) extending from the shaft 118 in order to move the locking element 130 distally toward the outer housing 116.

As seen in FIG. 3, the locking element 130 includes an engaging face 132 with a first plurality of ratchet teeth 134. The outer housing 116 includes a handle portion 122 having a contacting face 124 with a second plurality of ratchet teeth 126. The ratchet teeth 126 of the contacting face 124 are sized and dimensioned to correspond with the first plurality of ratchet teeth 134 of the engaging face 132 of the locking element 130. The ratchet teeth 126, 134 are also sized and dimensioned such that a ratcheting mechanism occurs when the contacting face 124 of the handle portion 122 contacts or engages the engaging face 132 of the locking element 130. Accordingly, when the engaging face 132 of the locking element 130 contacts and mates with the contacting face 124 of the handle portion 122, the shaft 118 is able to ratchet or rotate in a uni-directional rotation.

The locking element 130 includes a locking button 136 integrated with and disposed within the locking element 130. The locking button 136 is configured to engage at least one notch 140 formed along the periphery of the shaft 118. The notch 140 includes a flat face 146 such that when the locking button 136 is retained in the notch 140 (shown in FIG. 5); the locking element 130 is retained in position and unable to move longitudinally along the length of the shaft 118. Thus, when the locking button 136 is engaged and retained in the notch 140, the first plurality of ratchet teeth 134 on the engaging face teeth 132 are separated a distance from the second plurality of ratchet teeth 126 on the contacting face 124 and the ratcheting mechanism is not engaged. In this configuration, the shaft 118 is able to freely rotate in both directions (e.g., clockwise and counterclockwise) to tighten or loosen the fastening element.

The locking button 136 may be engaged with the notch 140 (the ratcheting mechanism is not engaged and the instrument 100 is "unlocked") or unengaged in the notch 140 (the ratcheting mechanism is engaged and the instrument 100 is "locked") by depressing the locking button 136. A spring 142 may be configured to assist in engaging and unengaging the locking button 136 in the notch 140. When the locking button 136 is depressed, the locking button 136 is no longer secured in the notch 140 and the spring 138 moves the locking element 130 distally toward the outer housing 116, the handle 122, and the contacting face 124. Thus, when the locking button 136 is not engaged in the notch 140 (as shown in FIG. 4), the first plurality of ratchet teeth 134 on the engaging face 132 are contacting and mating with the second plurality of ratchet teeth 126 on the contacting face 124 and the ratcheting mechanism is engaged. The spring 138 may be configured to keep the ratcheting mechanism engaged unless the locking button 136 is again depressed.

By way of example, with the driver 100 in the unlocked position, the user can attach a screw by threading the instrument shaft 118 into the screw. Once tight, the lock can be engaged by pressing the locking button 136. The locking button 136 releases the locking element 130, which is forced forward via the spring 138. The locking element 130 slidably engages with the threaded shaft 118. The locking element 130 and, in particular, engaging face 132 will prevent counter-clockwise rotation, but still allows the instrument 100 to be further tightened. This is accomplished via the uni-directional ratchet. This design has several benefits over the current technology including, for example, a secure lock with the added advantage of in-situ tightening without an additional step.

According to another embodiment, FIGS. 6-12 depict alternate views of a surgical instrument 200 (also called an inserter 200) suitable for inserting a surgical device, such as an implant. In addition, the surgical instrument 200 provides for a simple, highly repeatable method for in-situ implant assembly. The instrument 200 incorporates numerous mechanisms to increase the function and safety of the inserter 200, without complicating the process of assembly and providing a secure method of assembly in-situ. Each component works together to create an instrument 200 that provides the user with a safe and repeatable assembly method.

Figure 6A:
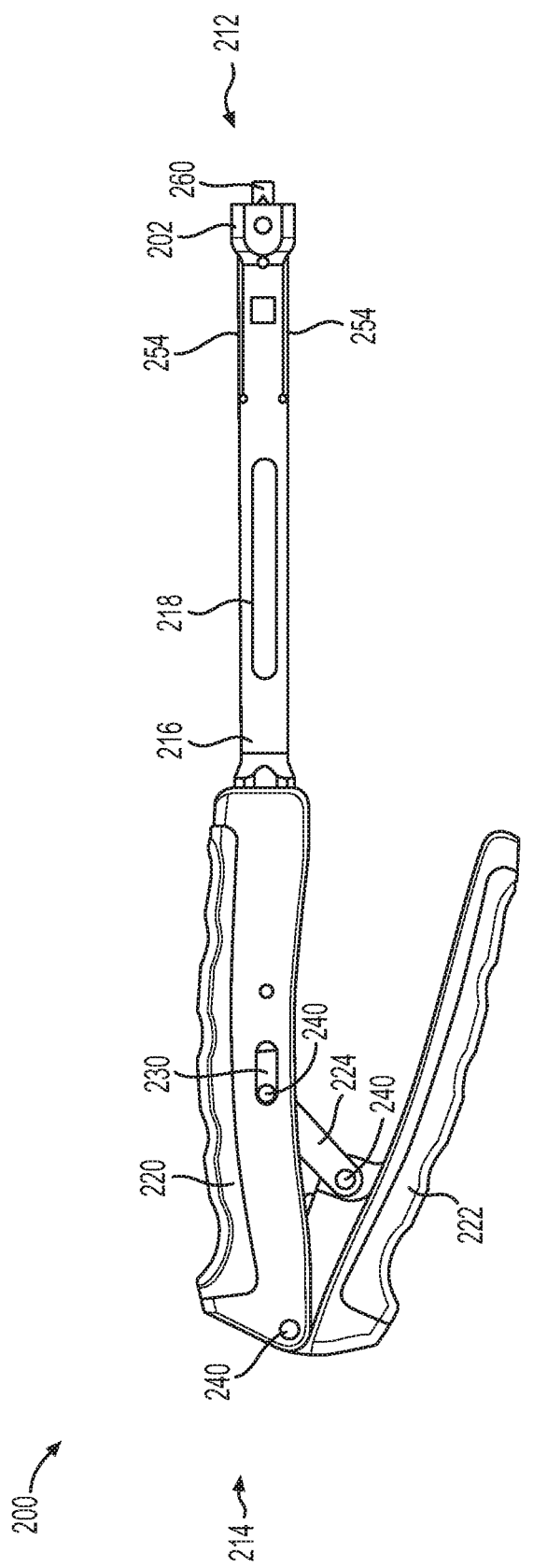
FIG. 6A shows a side view of an instrument suitable for inserting an implant according to one embodiment.
Figure 6B:
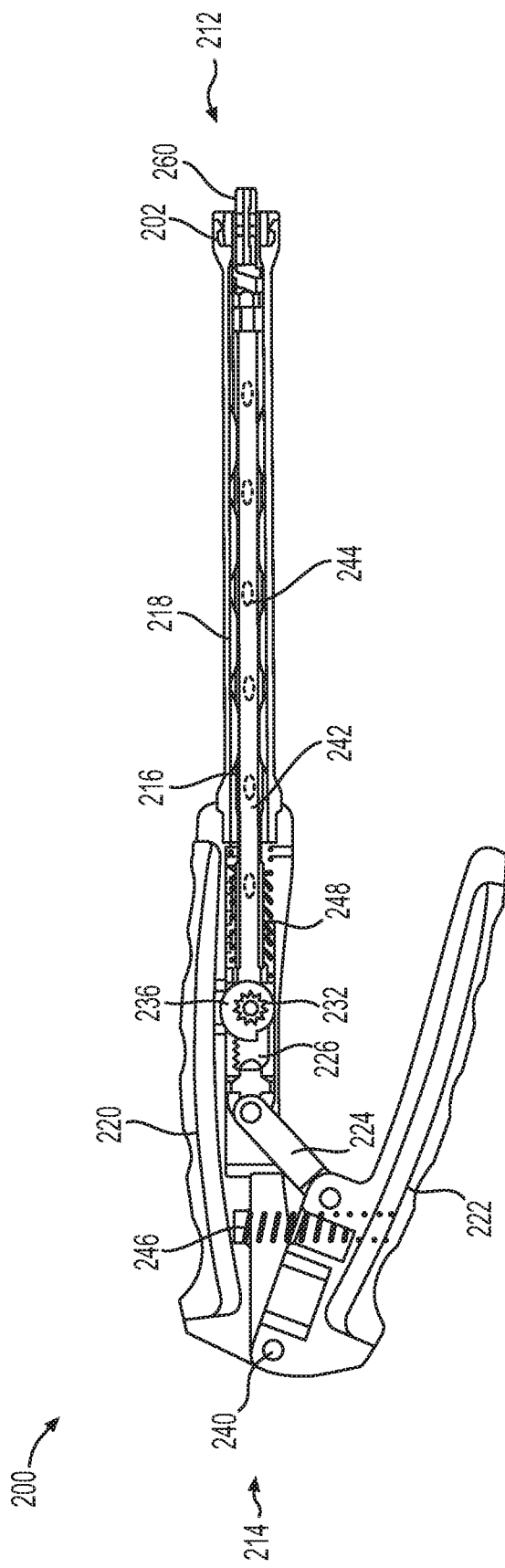
FIG. 6B shows a cross-sectional view of the inserter instrument shown in FIG. 6A.

As shown in FIGS. 6A and 6B, the instrument 200 includes a body 216 having an outer longitudinal housing or retention shaft 218, a handle 220, and a trigger 222. The body 216 holds all of the components and keeps them aligned as well as providing a palm support. The inserter 200 may be attached or affixed to any suitable arms, handles, frames, devices, or the like known in the art. The handle 220 or handles (including trigger 222) may be configured such that an operator is able to maneuver the inserter 200 in a suitable manner. In particular, the trigger 222 may be connected to the handle 220 by coupling element 240, which allows for rotational motion such that the trigger 222 and the handle 220 may be squeezed together and released apart. In addition, a spring 246 may be provided between the handle 220 and the trigger 222 to allow for the trigger 222 to maintain an expanded position unless a force is applied. Thus, the handle 220 and the trigger 222 provide a mechanism for application of a force.

The body 216 of the instrument 200 includes the outer longitudinal housing or retention shaft 218. The retention shaft 218 includes a generally cylindrical longitudinal body. The retention shaft 218 is generally hollow and defines a channel extending longitudinally therethrough. The retention shaft 218 includes a distal tip 202 adapted to receive and mate with a portion of an implant component, bony fixation point, and/or bone fastener including a screw, tulip, yoke, or the like. The retention shaft 218 is designed to accept the implant that is to be delivered to the surgical site.

Figure 7B:
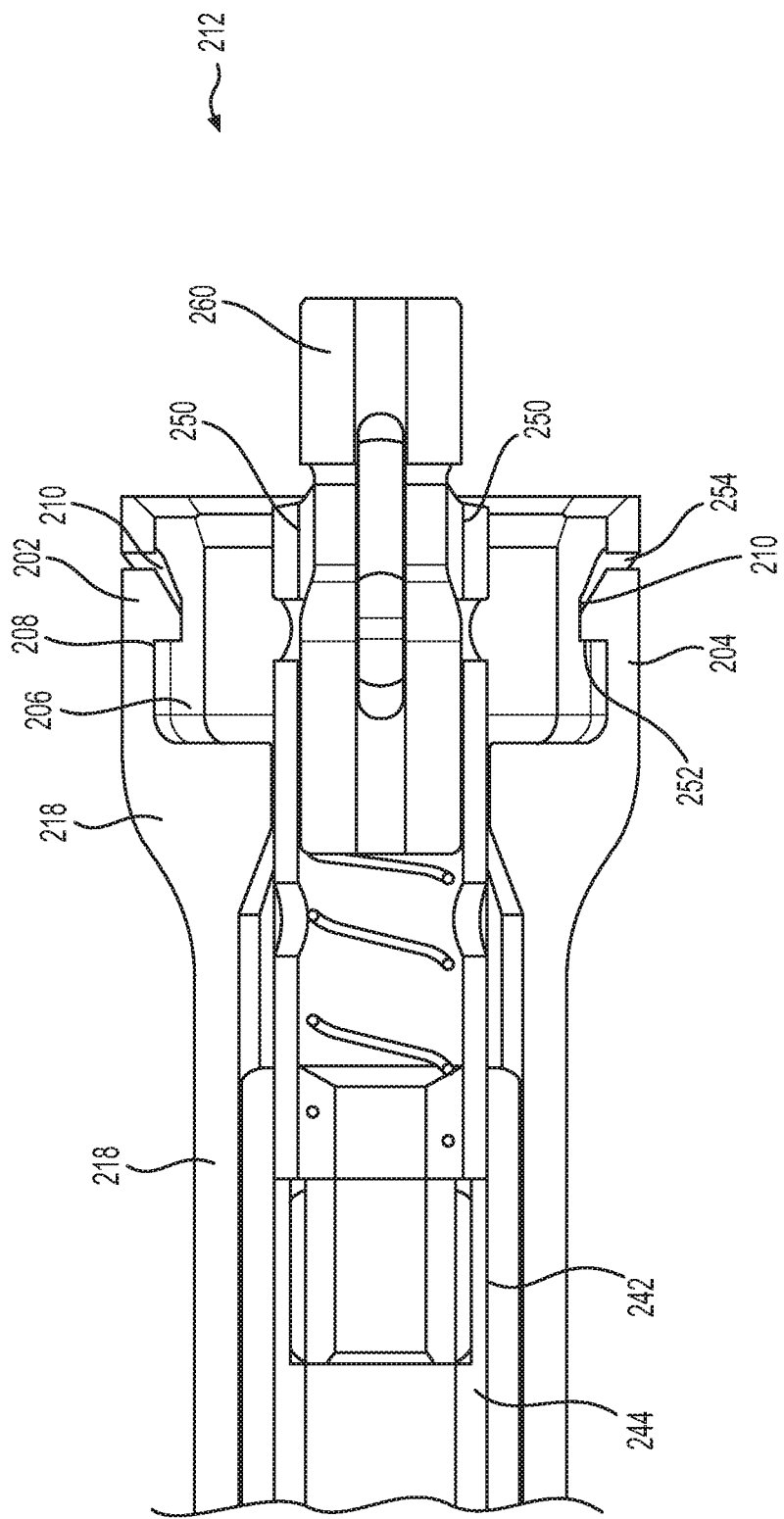
Figure 8B:
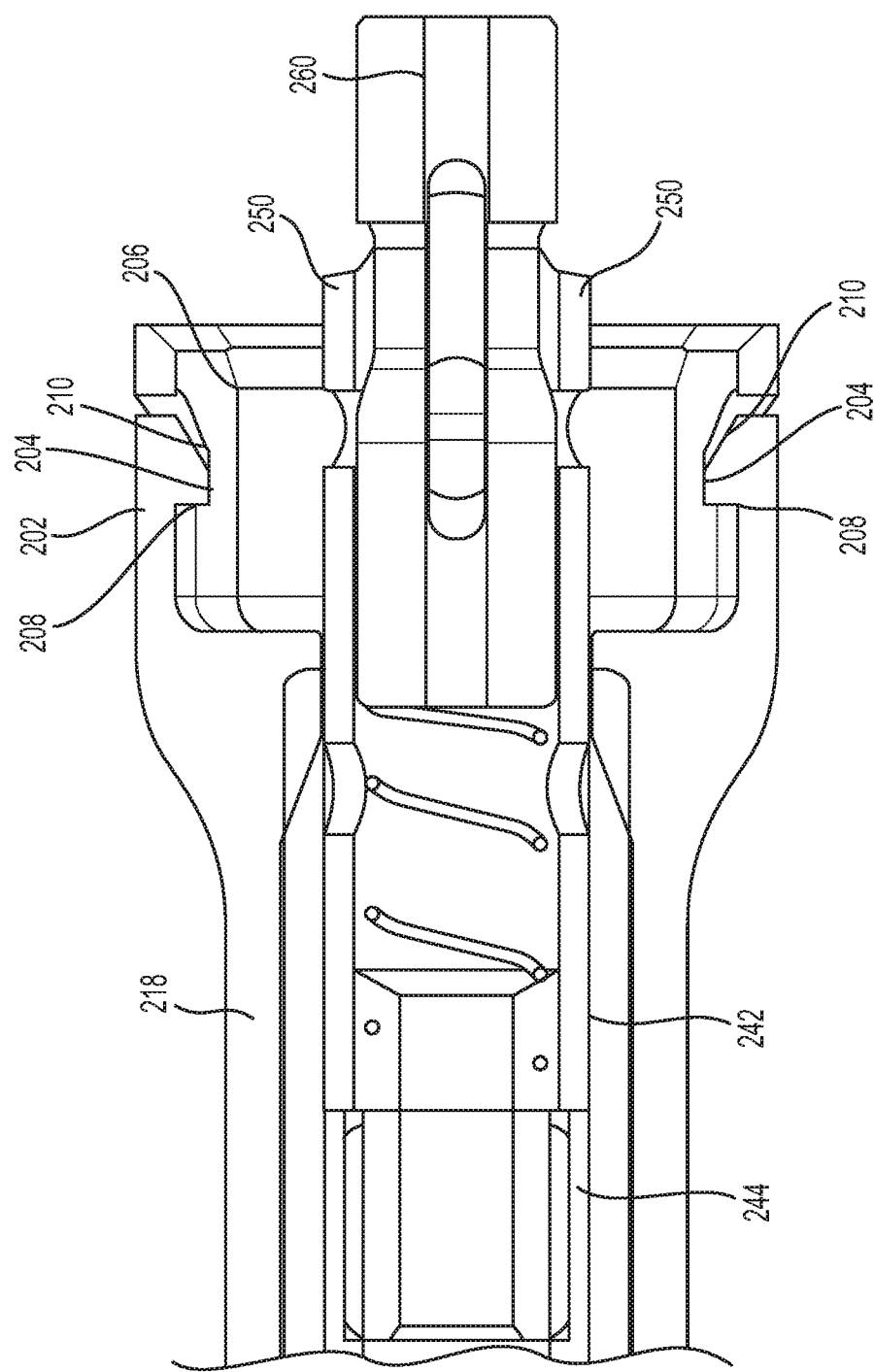
Figure 9A:
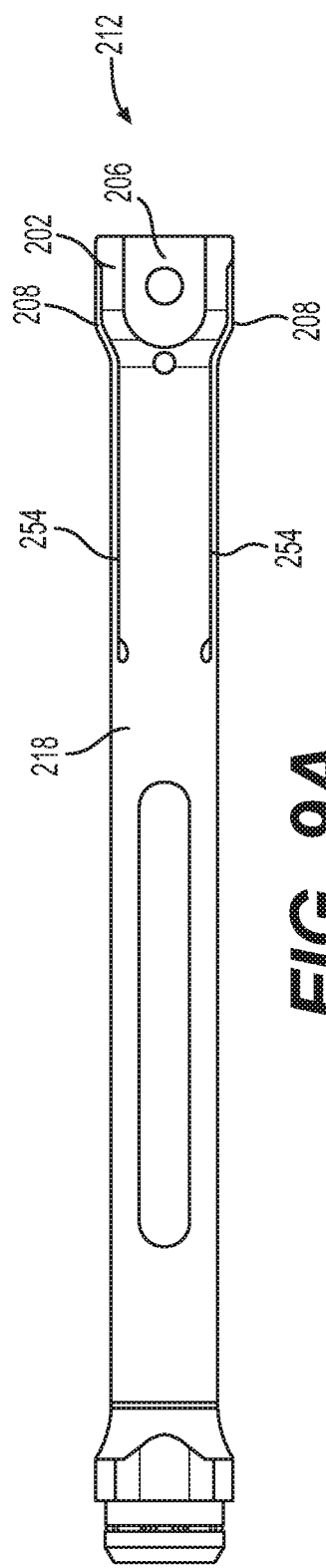
FIGS. 9A-9C show alternate views of a retention shaft suitable for use with the inserter instrument depicted in FIG. 6A.
Figure 9B:
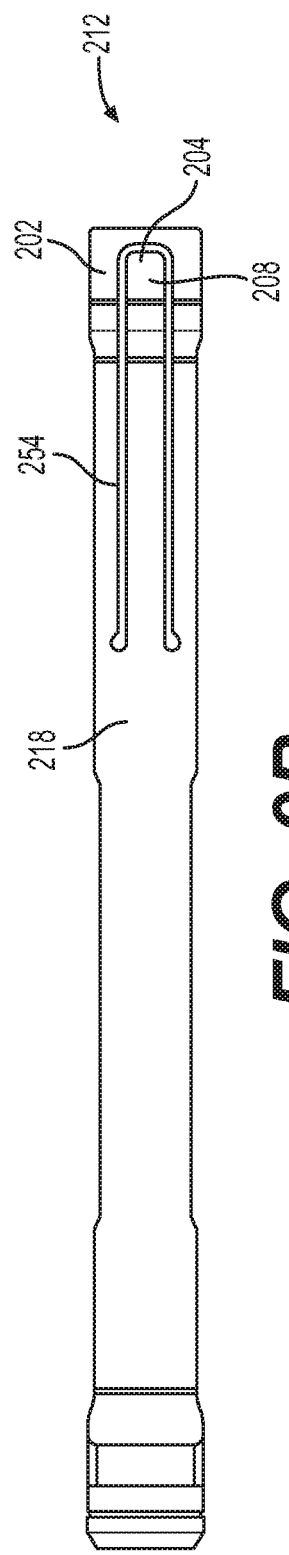
Figure 9C:
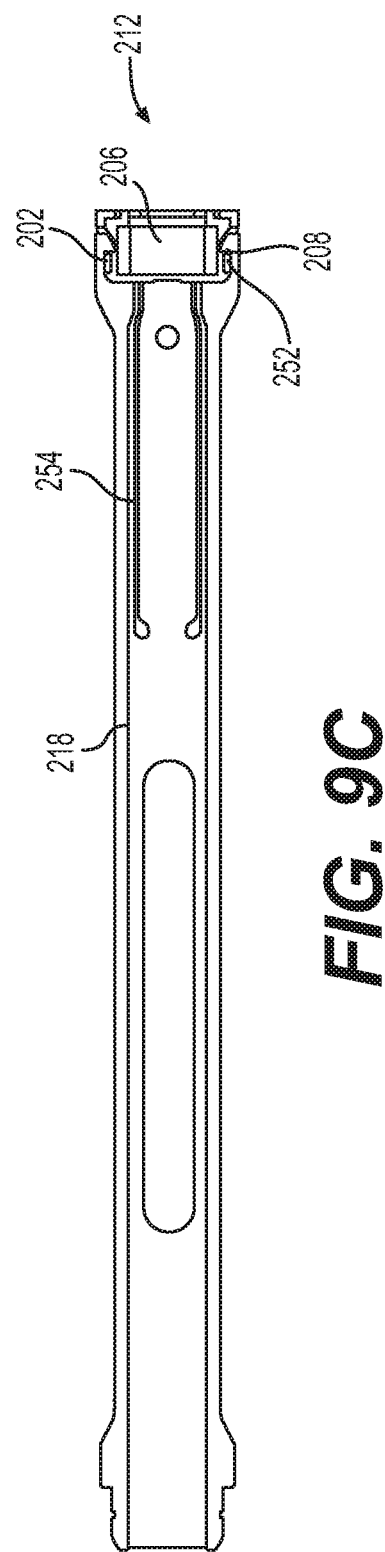
Figure 10A:
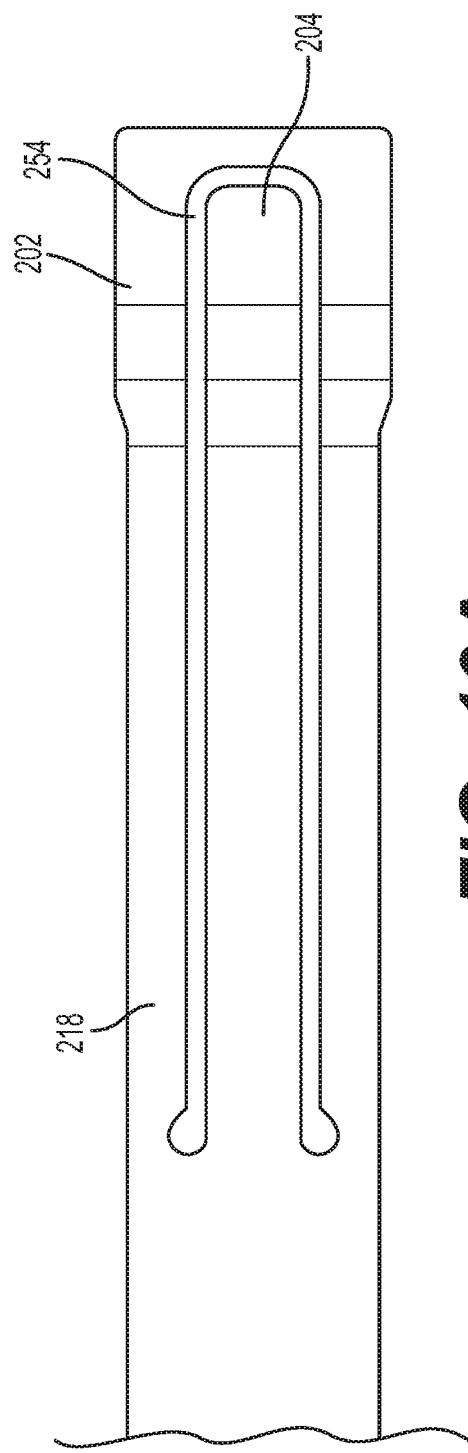
FIGS. 10A and 10B show close-up views of the retention shaft and distal tip shown in FIGS. 9B and 9C, respectively.
Figure 10B:
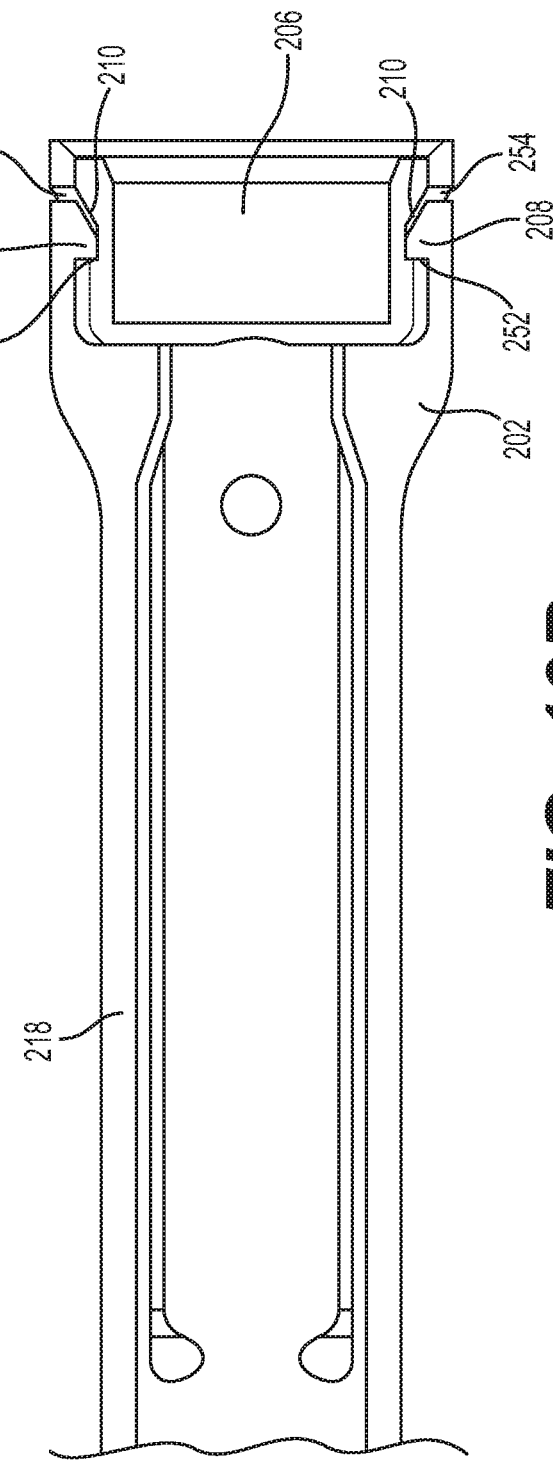

The distal tip 202 is mateable with the intended component, such that, when assembled, the distal tip 202 and the intended component create a rigid or semi-rigid assembly. As shown in FIGS. 7B and 8B, the distal tip 202 includes an interior wall 206 which defines one or more catches 208 that are adapted to mate with at least a portion of an implant component, etc. For example, the catches 208 may have a shape that complements or corresponds to the shape of the outer surface of the implant component, bony fixation point, and/or bone fastener. In particular, an embodiment of the retention shaft 218, depicted in FIGS. 9A-9C, is suitable to mate with a modular tulip. These catches 208 may include a spring tab 204 and may include a ramped surface 210. In particular, two spring tabs 204 at the distal end 212 may form a snap fit between the implant and instrument 200. These tabs 204 flare open to accept and hold the implant. These tabs 204 are pushed open by the release shaft 244 when the trigger 222 on the handle 220 is fully depressed, releasing the implant.

The retention shaft 218 is sized and shaped to receive a locking shaft 242 and a release shaft 244 therein. In particular, the locking shaft 242 is pinned to the linkage 224 such that when the linkage 224 moves (e.g., due to a small squeezing force), the linkage 224 moves linearly in the opening 230 of the handle 220 to move the entire shaft 224 distally and fully secure the implant. The locking shaft 242 provides an axial force to internal components of the mating implant, rigidly attaching the implant components together. The release shaft 244 and locking shaft 242 may extend in any suitable configuration through the retention shaft 218 in order to perform the intended functions. The release shaft 244 is responsible for the bulk of the instrument 200 function providing the lock and release features.

The release shaft 244 also moves through the body 216 via the linkage 224 between the trigger 222 and the handle 220. A first end of the linkage 224 is connected to a portion of the trigger 222 via a coupling element 240, and a second end of the linkage 224 is connected to a portion of the handle 220 via another coupling element 240. In particular, the coupling element 240 provided at the second end of the linkage 224 may be retained in a longitudinal opening 230 in the handle 220. The longitudinal opening 230 allows for the rotational motion provided by squeezing the trigger 222 to be converted to linear motion of the release shaft 244.

Figure 7A:
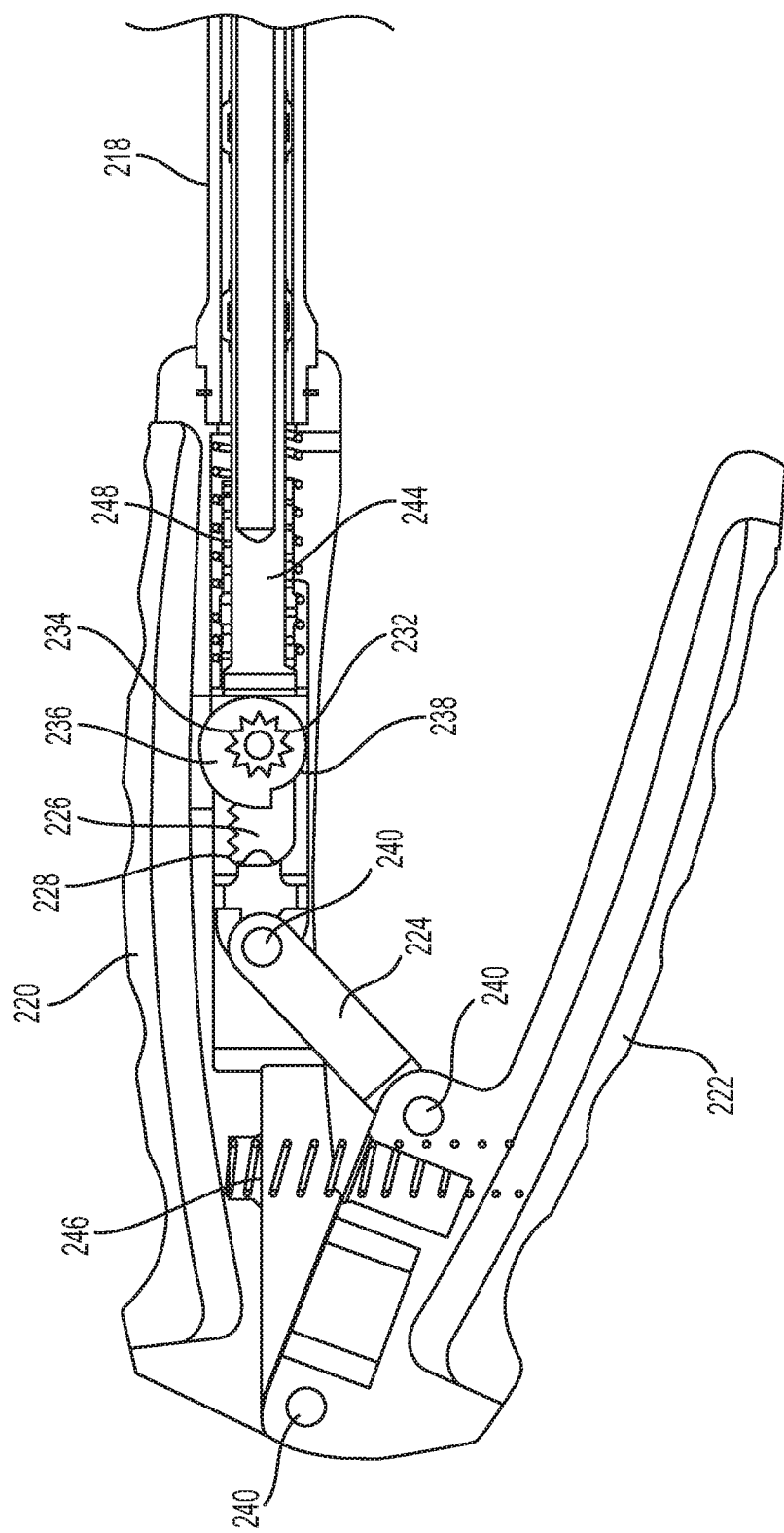
FIGS. 7A and 7B show close-up views of portions of the inserter instrument shown in FIG. 6B with the trigger in an expanded position.

As shown in FIG. 7A, the release shaft 244 has an integrated rack 226 and houses the pinion 232, cam 236, and locking shaft 242. The integrated rack 226 has a longitudinal body and includes a plurality of teeth 228 on at least one side of the rack 226. The pinion 232 has a wheel-like body with a plurality of teeth 234 positioned along the periphery of the body and which radially extend outward. The cam 236 include a wheel-like or substantially circular body and includes at least one projection 238. The cam 236 is rotatably attached to the pinion 232, which rotates relative to the linear motion of the rack 226. The axial force is delivered through the rotation of cam 236. The pinion gear 232 may be coupled with a coupling element to allow for a pivot point and rotational motion of the pinion 232 and the cam 236.

The pinion 232 translates the linear movement from the rack 226 to a rotational motion of the cam 236. The pinion 232 is pinned to the body 216 and rotates relative to the release shaft 244. Thus, the teeth 228 of the integrated rack 226 are configured to contact and rotate the pinion 232, and the pinion 232 is configured to rotate the cam 236 to cause linear movement of the release shaft 244 and/or locking shaft 242.

When the trigger 222 is in an expanded configuration relative to the handle 220, for example, as depicted in FIG. 7A, the locking shaft 242 and release shaft 244 are in a retracted position. As is evident, the projection 238 on the cam 236 is not contacting the release shaft 244. When the trigger 222 is partially depressed, the linkage 224 moves linearly in the opening 230 of the handle 220 to move the locking shaft 242 distally in order to provides an axial force to and rigidly secure the mating implant. FIG. 7B depicts the distal end 212 of the inserter 200 when the trigger 222 is in the expanded configuration. With the release shaft 244 in a retracted state, one or more tabs 250 do not extend beyond a distal face of the distal tip 202. Thus, if engaged, an implant would remain engaged with the retention shaft 218.

Figure 8A:
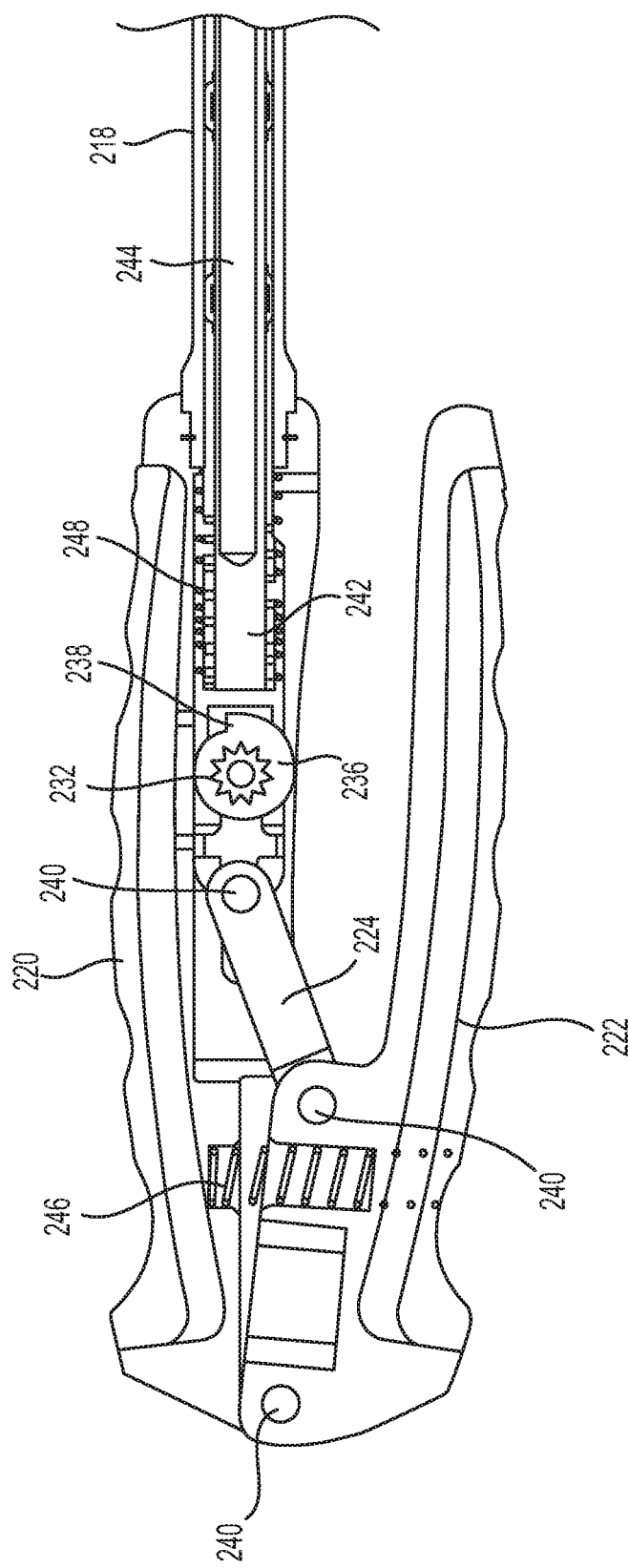
FIGS. 8A and 8B show close-up views of portions of the inserter instrument shown in FIGS. 7A and 7B with the trigger depressed.

When the trigger 222 is completely depressed, as shown in FIG. 8A, the linkage 224 continues to move linearly in the opening 230 of the handle 220 and the teeth of the rack 226 mate with the teeth 234 on the pinion 232 to rotate the pinion 232 and the cam 236. The projection 238 on the cam 236 rotates to contact and move the release shaft 244 distally to provide the release shaft 244 in a fully extended position. A spring 248 may also be provided around the release shaft 244 to move the release shaft 244 in the distal direction. FIG. 8B depicts the distal end 212 of the inserter 200 when the trigger 222 is in the compressed configuration and the release shaft 244 is extended. With the release shaft 244 in an extended state, the tabs 250 extend beyond a distal face of the distal tip 202. Thus, if previously engaged, an implant would become disengaged from the retention shaft 218.

By way of example, the surgical site may include a pedicle anchor or alternative means of bony fixation (e.g., sacral plate, lamina clamp, lamina band, etc.). The instrument 200 operates by first collecting an implant component (not shown). The implant component is attached to the distal tip 202 of the inserter instrument 200, which is then moved to a surgical site. The implant is attached temporarily to the preferred bony fixation method using axial force. Once the desired position is achieved, the trigger 222 on the handle 220 may be pulled, locking the implant to the chosen fixation method. Pulling of the trigger 222 on the handle 220 will also release the instrument from the implant in order to leave the implant securely assembled in-situ.

Unlike traditional devices which rely on snap-fits and material properties to ensure a safe method of assembly, the inserter 200 uses a change in implant state as well as mechanical force to ensure the implant components are properly mated. For example, with the bony fixation point already placed, the inserter 200 attaches to the mating component and holds it securely. The implant is held in the retention shaft 218 by displacing the spring tabs 204 on the sides of the shaft 218. The instrument 200 is used to approximate the mating implant to the bony fixation point. The mating implant is temporarily attached using axial force. The implant is permanently attached by pulling the trigger 222 of the instrument handle 220.

The action of pulling the handle 220 performs several operations. The trigger 222 of the handle 220 may actuate the linkage 224 attached to the release shaft 244, which causes linear motion, collinear to the retention shaft 218. The release shaft 244 has an integrated rack 226 housed within the body 216. This rack 226 is mated with a pinion gear 232 which is rotatably mated with a cam 236 and the body 216. The pinion gear 232 will rotate relative to the linear motion of the release shaft 244, which rotates the cam 236. This cam 236 is slidably attached to the locking shaft 242, which when rotated, provides axial force to the locking shaft 242, locking the mating implant. The release shaft 244 continues to articulate linearly until it comes in contact with two ramped surfaces 210 on the inside of the spring tabs 204. The release shaft 244 will deflect the spring tabs 204 allowing the mating implant to be released.

The inserter 200 may further include a safety lock 260. The safety lock 260 is a separate mechanism that locks the instrument 200 unless the bony fixation point is within the mating implant body. The lock 260 may have any suitably shaped body and form, such as tubular, elongated projection, a pin, a protrusion, or the like which extends beyond the distal end of the distal tip 202. The lock 260 protrudes into the mating implant and must be pressed, releasing the instrument lock. Pressing the lock piston will articulate a separate piston via a pin slider mechanism, causing a motion approximately normal to the motion of the lock piston.

Figure 12:
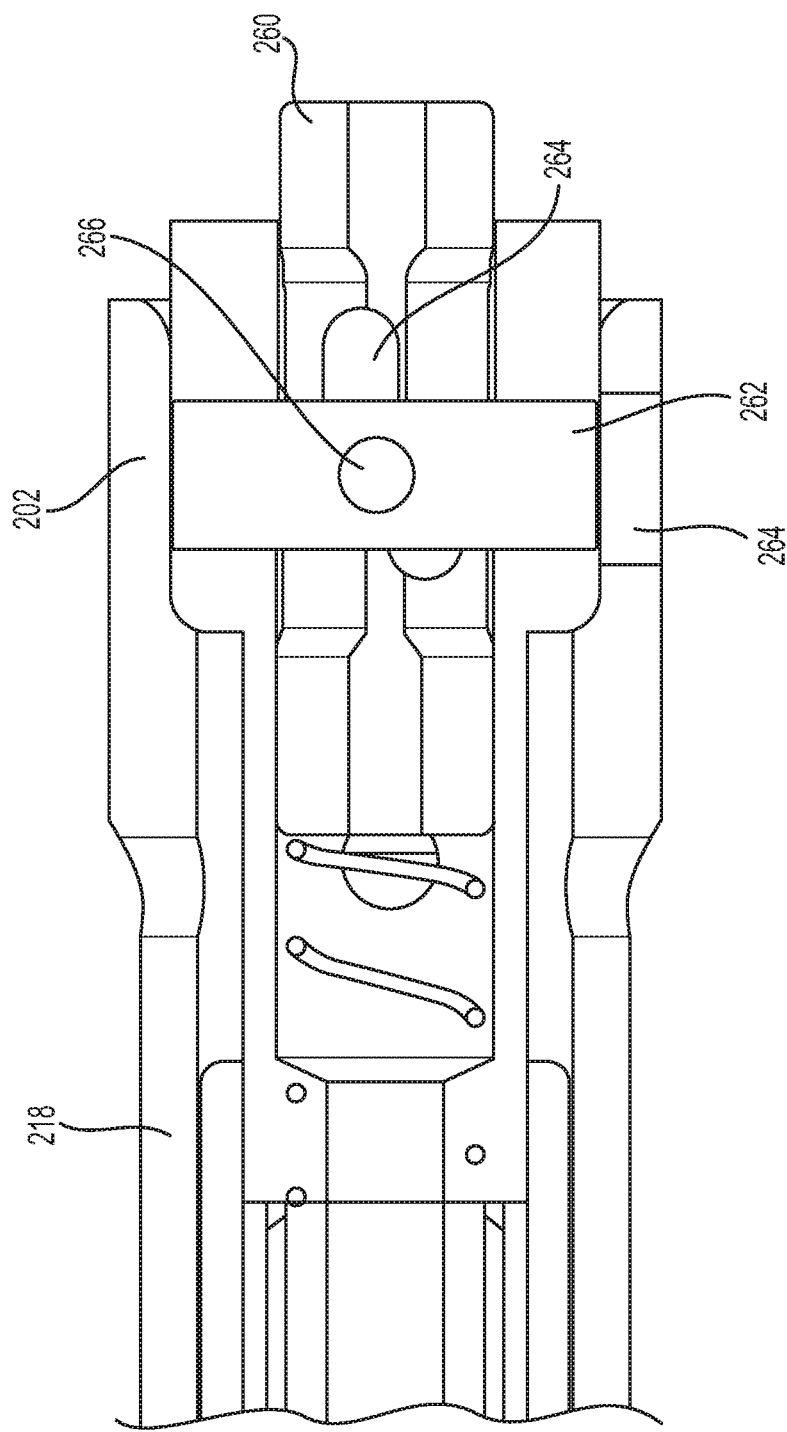
FIG. 12 shows the locking mechanism depicted in FIG. 11A in an unlocked state.

The safety lock 260 utilizes a pin 262 and follower 264 to provide the safety lock 260 at the tip of the instrument 200. The lock 260 is coupled to the pin 262 and positioned within the follower 264 via a coupling element 266, such as a pin. As best shown in FIG. 11C, the lock 260 includes the follower 264 which is a non-linear opening formed therein (e.g., an angled, v-shaped, or stepped configuration). The follower 264 opening is especially configured to translate the movement of the lock 260 in a proximal direction to a perpendicular movement for the pin 262. In a locked state, the pin 262 is housed in an opening 264 in the wall of the distal tip 202. When the pin 262 is engaged in the opening 264, as shown in FIG. 11A, the trigger 222 is locked and the instrument 200 cannot be used. This prevents a user from using the instrument 200 if it is not properly seated. When the safety lock 260 is depressed (e.g., when an implant is secured thereto), as shown in FIG. 12, the coupling element 266 follows the follower 264 and allows the pin 262 to retract from the opening 264 in the distal tip 202. This enables full functionality of the instrument 200.

According to another embodiment, the instruments described herein may be provided with a secure form of interaction between implants and instruments. Although exemplified for inserter instrument 200, the attachment mechanisms described herein may be applied to any suitable surgical instrument including, but not limited to, correction, reduction, persuasion, insertion, removal, manipulation (compression, distraction, etc.), instruments to implant interaction, instruments to instrument interaction, implant to implant interaction, etc.

As shown in FIGS. 9A-9C, the retention shaft 218 includes the distal tip 202, which is mateable with the intended component, such that, when assembled, the distal tip 202 and the intended component create a rigid assembly. The distal tip 202 includes an interior wall 206 which defines one or more catches 208 that are adapted to mate with at least a portion of an implant component, etc. These catches 208 may be in the form of a solid ledge 252 and one or more spring cuts 254 to form a rigid form of interaction between the implant component and the instrument. The spring cuts 254 and solid ledge 252 may help to address the issue of inadequate retention force and reduce the likelihood that the instrument becomes disassociated from the implant. The implant component may contain similar reciprocal ledges or projections to engage the solid ledge 252, for example.

The catches 208 may include a spring tab 204. One or more spring cuts 254 may be formed through the instrument allowing the catch 208 to flex outwardly and radially away from the instrument. The spring cut 254 may be in the form of a U-shaped design to allow a greater area of the catch 280 to deflect. The spring cut 254 may include one or more flat sections or portions or may be of any suitable shape, cross-section, or design. The spring cuts 254 may be designed to allow the spring tabs 204 to flex when the surgical device is secured or released from the instrument. The other outer surfaces may be immovable while the spring tabs 204 allow the implant to be inserted and released. Thus, the outer body remains rigid relative to the holding features. By way of example, two spring tabs 204 at the distal end 212 may form a snap fit between the implant and instrument. These tabs 204 flare open to accept and hold the implant. The tabs 204 may also be pushed open when the implant is released.

The catches 208 may include one or more inner ledges 252 designed to mate with the surgical device. This allows for the mating implant to be inserted and retained securely. These form-fitting mating inner surfaces may help to create a semi-rigid or rigid interface with the mating implant. The catches 280 may also include the ramped surface 210 to facilitate an axial insertion of the surgical device onto the instrument (e.g., a snap-fit). This design has several benefits including an enhanced implant/instrument interface including a more rigid connection and simpler insertion and removal.

Figure 14A:
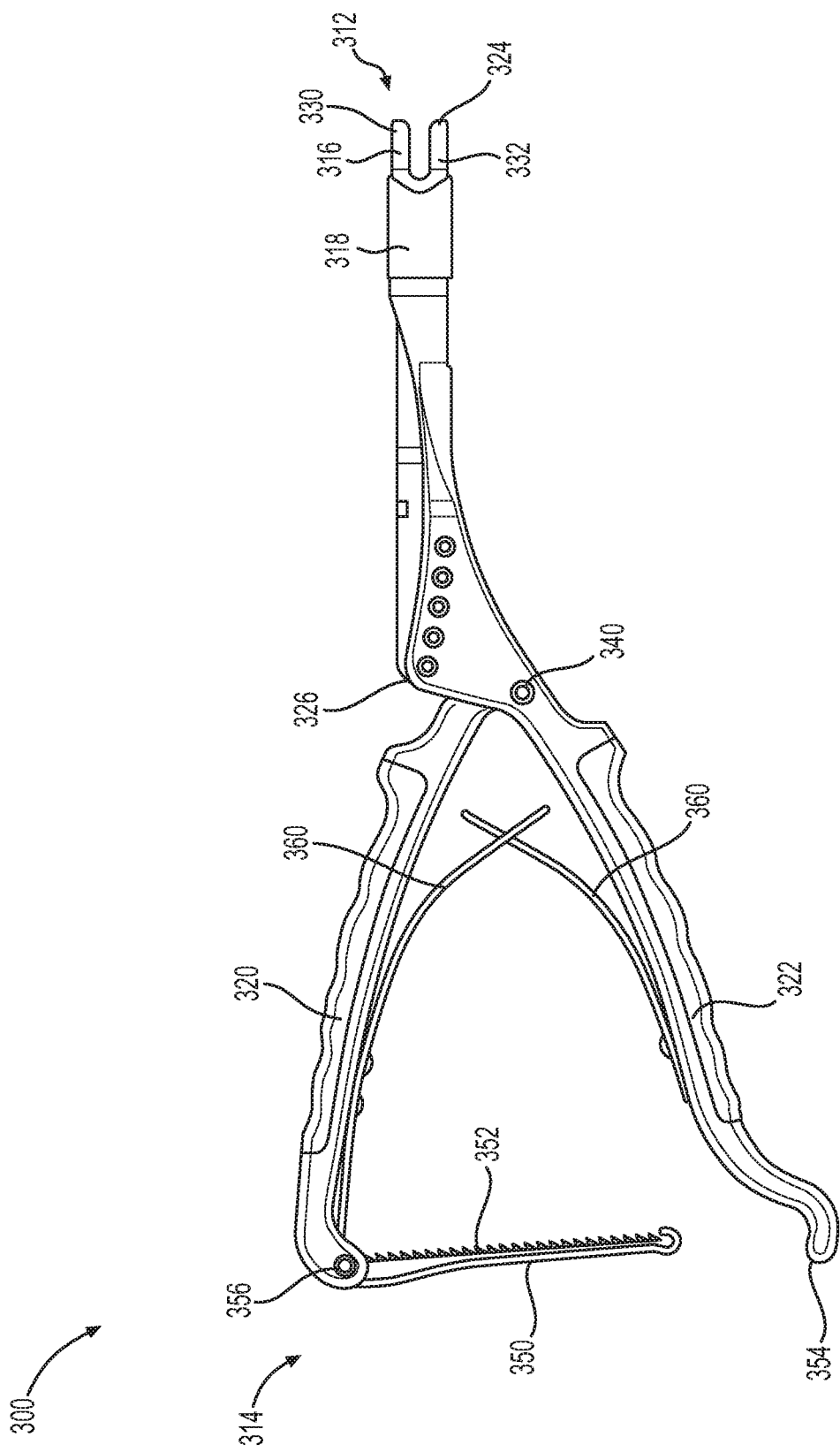
Figure 15A:
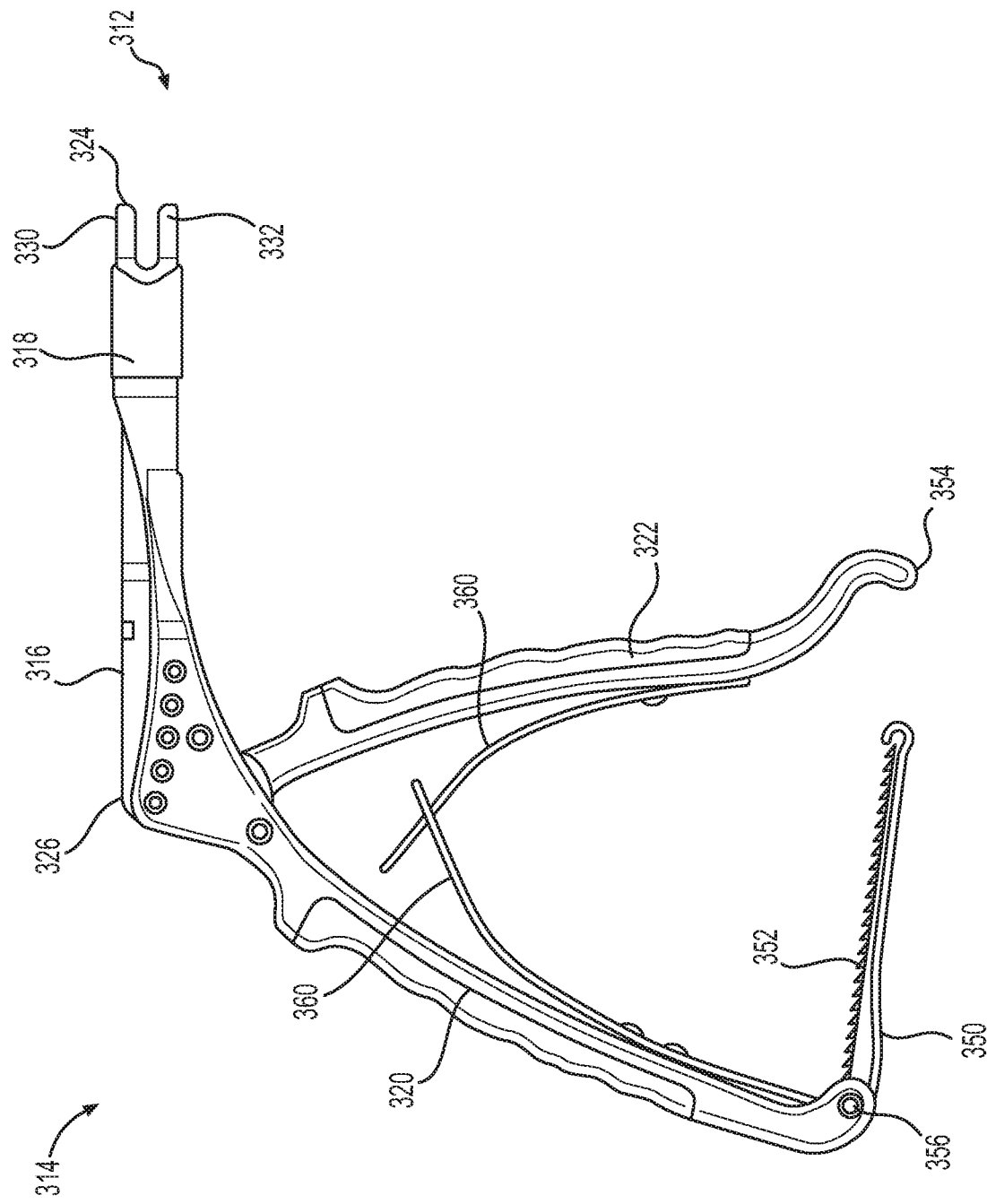

According to another embodiment, FIGS. 14A and 15A depict side views of instruments 300 (also called reducers 300) suitable for persuading together a rod and a seat recess of an orthopedic device or coupling element, such as a pedicle screw assembly including a fastener, tulip, yoke, or the like. In particular, the instruments 300 include reducing instruments suitable for aligning misaligned vertebrae.

As shown in FIG. 14A, the instruments 300 include a reducing member 316, an outer longitudinal body 318, and a handle or grip made including a first trigger element 320 and a second trigger element 322. The reducing member 316 includes a generally cylindrical longitudinal body. The reducing member 316 and has a working end 324 and a trigger end 326 extending from a distal end 312 toward a proximal end 314.

In addition, the reducing member 316 is generally hollow and defines a channel extending longitudinally through it from the working end 324 to the trigger end 326. The working end 324 of the reducing member 316 is adapted to receive a portion of a bone fastener including a tulip, yoke, or the like. In particular, the working end 324 is adapted to mate with an instrument or device, such as a fastener (e.g., a screw), a tulip, a rod, or the like. In this regard, the working end 324 may be forked and made up of a pair of opposing prongs 330, 332. The prongs 330, 332 each have an interior wall which defines one or more catches (not shown) that are adapted to mate with at least a portion of a pedicle screw assembly. These catches may include the spring tabs 204 and ramped surfaces 210, as discussed above. For example, the catches may have a shape that complements or corresponds to the shape of the outer surface of a receiver element, fastener, tulip, yoke, or coupling element.

The outer longitudinal member 318 has a body which is generally hollow and defines a channel extending longitudinally through it and is sized and shaped to receive the reducing member 316 therein. The outer longitudinal member 318 may be contiguous with the first or second trigger elements 320, 322. As shown in FIG. 14A, the longitudinal member 318 may be a single continuous extension of the second trigger element 322. In the embodiment shown in FIG. 15A, the longitudinal member 318 may be a single continuous extension of the first trigger element 320. The orientation of the outer longitudinal member 318 to the first and second trigger elements 320, 322 may depend on the approach taken by the surgeon. For example, in the embodiment depicted in FIG. 14A, the first and second trigger elements 320, 322 are generally co-planar with the longitudinal member 318 and reducing member 316. In FIG. 15A, on the other hand, the first and second trigger elements 320, 322 are generally perpendicular with respect to the longitudinal member 318 and reducing member 316.

The reducing member 316 may be able to translate or move with respect to the outer longitudinal member 318 when a force is applied to the handle, namely, to either or both of the first and second trigger elements 320, 322. In particular, when a force is applied to either or both of the first trigger element 320 and the second trigger element 322 the reducing member 316 may move proximally, for example, with respect to the longitudinal member 318 or generally with respect to the instrument 300. By moving in this manner, the reducing member 316 is able to re-align one or more misaligned vertebrae and move a seat recess of an orthopedic device or coupling element, such as a pedicle screw assembly including a fastener, tulip, yoke, or the like, into position to be coupled to a rod or the like.

The reducing member 316 proximate to the trigger end 326 has a first plurality of gear teeth 336. For example, the reducing member 316 may comprise a substantially flat portion 334 proximate to the trigger end 326. The flat portion 334 may comprise the first plurality of gear teeth 336. These gear teeth 336 may extend along the entire flat portion 334 or a portion thereof. Similarly, the first plurality of gear teeth 336 may extend from the trigger end 326 along a length of the reducing member 316 or may extend along a portion thereof.

Figure 15B:
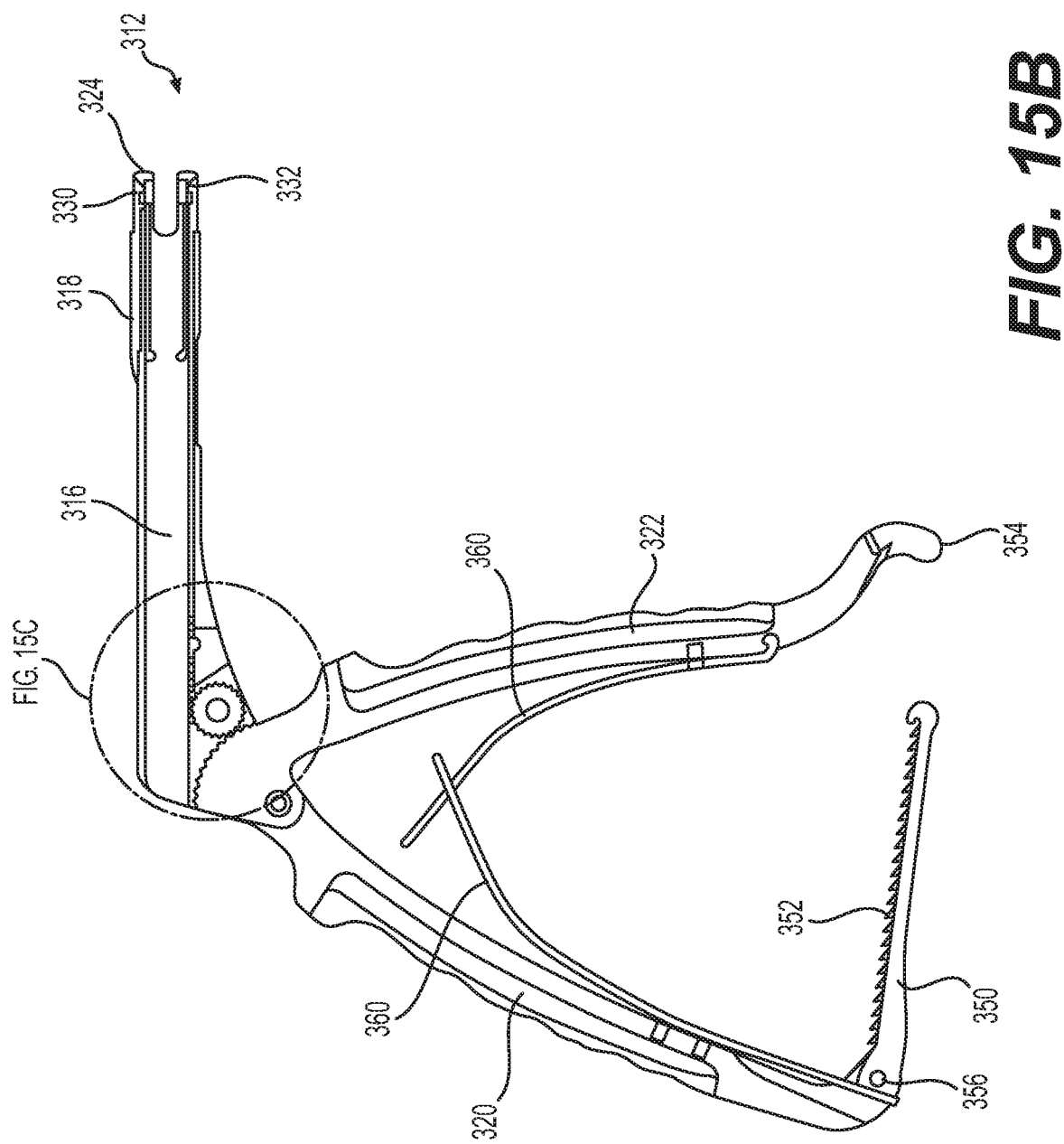

As can be seen in FIGS. 14B and 15B and with close up views in FIGS. 14C and 15C, the handle of the instrument 300 includes at least a first trigger element 320 and a second trigger element 322, and at least one of the trigger elements 320, 322 includes a second plurality of gear teeth 338. The first and second trigger elements 320, 322 are coupled together with coupling element 340, which acts as a pivot point. Thus, when the first and second trigger elements 320, 322 are moved relative to one another or squeezed together in the direction of arrows A (see FIG. 14C), the movement of the trigger elements 320, 322 translates to linear motion for the reducing member 316 due to coupling element 340 and gear teeth 336, 338. The force causes movement of the reducing member 316 relative to the outer longitudinal body 318 such that the reducing member 316 slides through the outer longitudinal body 318 in the direction of arrow B. The process can be a single, continuous movement or alternatively can be a step-wise movement due to the use of a ratchet 350 described below.

As depicted in FIG. 14C, the second plurality of gear teeth 338 may be configured to directly engage and mate with the first plurality of gear teeth 336. Thus, when the first and second trigger elements 320, 322 are moved relative to one another (e.g., squeezed), the first trigger element 320 rotates in the direction of arrow C and the reducing member 316 moves proximally in the direction of arrow B. After the vertebrae or element has been reduced, the reducing member 316 is able to return to its original position such that the reducing member 316 moves distally in a direction opposite to arrow B and the first trigger element 320 rotates in a direction opposite to arrow C to return the first and second trigger elements 320, 322 to an expanded position.

In the embodiment depicted in FIG. 15C, the instrument 300 further includes a pinion gear 342. The pinion gear 342 has a wheel-like body with a plurality of teeth 344 positioned along the periphery of the body and which radially extend outward. The pinion gear 342 may be coupled with coupling element 346 to allow for a pivot point and rotational motion of the pinion gear 342. In this embodiment, the first and second gear teeth 336, 338 do not directly engage and mate together. The pinion gear 342 translates the movement from the second set of gear teeth 338 to the first set of gear teeth 336. Thus, the second plurality of gear teeth 338 are configured to contact and rotate the pinion gear 342, and the pinion gear 342 is configured to contact at least a portion of the first plurality of gear teeth 336 to cause the reducing member 316 to move proximally in the direction of arrow B.

When the first and second trigger elements 320, 322 are moved relative to one another (e.g., squeezed), the second trigger element 322 rotates in the direction of arrow C and the reducing member 316 moves proximally in the direction of arrow B. After the vertebrae or element has been reduced, the reducing member 316 again is able to return to its original position such that the reducing member 316 moves distally in a direction opposite to arrow B and the second trigger element 322 rotates in a direction opposite to arrow C to return the first and second trigger elements 320, 322 to an expanded position.

In the embodiments depicted the second plurality of gear teeth 338 are positioned on an end of the first or second trigger elements 320, 322, respectively. It should be understood, however, that the gear teeth 338 may be positioned at any appropriate location so long as the first and second trigger elements 320, 322 are able to translate motion to the reducing element 316. Similarly, the coupling element 340 is positioned at an offset and opposite to the first and second gear teeth 336, 338, but it will be understood by those skilled in the art that the coupling element 340 may be positioned at any suitable location in order to act as an appropriate fulcrum.

As shown in FIGS. 14B and 15B, the handle of the instrument 300 may further include a ratchet mechanism 350. The ratchet mechanism 350 may include an elongate member extending from an end of the first or second trigger elements 320, 322 and having a plurality of teeth 352 extending therefrom. On the opposite of the first or second trigger elements 320, 322, a connector 354, for example, in the shape of a notch or catch (not shown) may engage at least one tooth from the plurality of teeth 352 on the ratchet mechanism 350. In particular, the teeth 352 of the ratchet mechanism 350 may cooperate with the connector 354 as the trigger elements 320, 322 are squeezed together or towards one another. The teeth 352 may be step-wise engaged with the connector 354. As the successive teeth 352 engage with the connector 354, the first and second trigger elements 320, 322 are temporarily locked into place such that the first and second trigger elements 320, 322 may not move away from one another. If an additional squeezing force is applied to the first and second trigger elements 320, 322, however, the first and second trigger elements 320, 322 ratchet together. Thus, the operator is not required to continue to apply pressure to the trigger elements 320, 322 to maintain a given position. In operation, the user may grasp the instrument 300 in one hand, and the reducing member 316 may be moved proximally in the direction of B in a step-wise manner due to the use of the ratchet mechanism 350.

The ratchet mechanism 350 is connected to the first or second trigger elements 320, 322 with a suitable coupling element 356. This coupling element 356 allows the secondary ratchet mechanism to be pivoted out of position or alignment with the connector 354 if a ratcheting action is not required, no longer needed, or the reducing member 316 needs to be advanced toward a proximal position. The handle portion including the first and second trigger elements 320, 322 may further include one or more spring elements 360 positioned and configured to provide a spring-like action to extend the first and second trigger elements 320, 322 away from one another. A suitable spring device may be selected by one of ordinary skill in the art.

Each of the first and second plurality of gear teeth 336, 338, gear teeth 344 on the pinion gear 342, and ratchet teeth 352 on the ratchet 350 may comprise any suitable number or type of teeth, profile for the teeth (e.g., straight, curved), gear ratio, etc. as would be selected by one of ordinary skill in the art. The coupling elements 340, 346, 356 may also include any suitable coupling devices known in the art, such as pins, hinges, or the like which allow the components to pivot or swivel around an axis of rotation.

Figure 16:
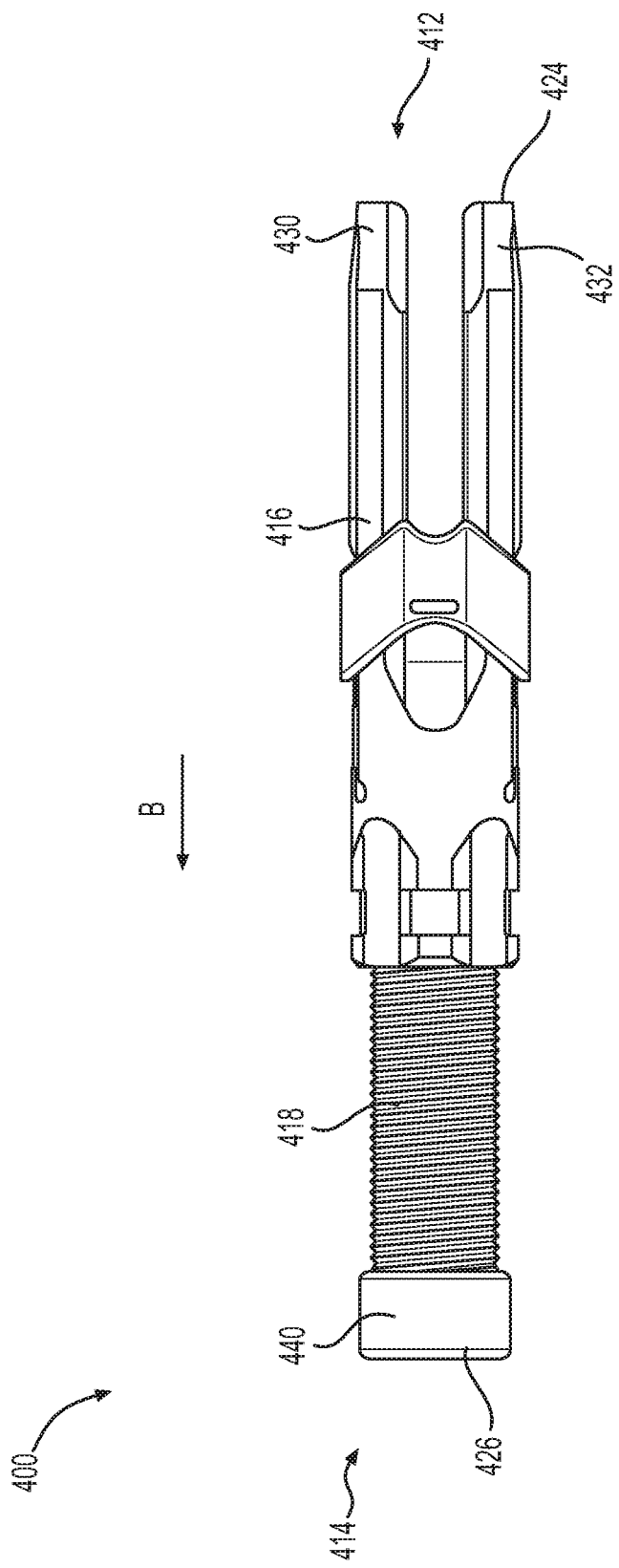
FIG. 16 depicts yet another embodiment of an instrument with a threaded reducer.

According to another embodiment, FIG. 16 depicts a threaded reducer 400. The threaded reducer 400 includes a reducing member 416 having a generally cylindrical longitudinal body and a threaded portion 418 with at least a partially helical thread. The reducing member 416 and has a working end 424 and a proximate end 426 extending from a distal end 412 toward a proximal end 414. The reducing member 416 is generally hollow and defines a channel extending longitudinally through it from the working end 424 to the proximate end 426.

The working end 424 of the reducing member 416 is adapted to receive a portion of a bone fastener including a tulip, yoke, or the like. In particular, the working end 424 is adapted to mate with an instrument or device, such as a fastener (e.g., a screw), a tulip, a rod, or the like. In this regard, the working end 424 may be forked and made up of a pair of opposing prongs 430, 432. The prongs 430, 432 each have an interior wall which defines one or more catches (not shown) that are adapted to mate with at least a portion of a pedicle screw assembly. These catches may include the spring tabs 204 and ramped surfaces 210 discussed above. For example, the catches may have a shape that complements or corresponds to the shape of the outer surface of a receiver element, fastener, tulip, yoke, or coupling element.

The reducing member 416 may be able to translate or move, for example, in a proximal direction when a rotation force is applied to the handle 440. As a torque is applied to the handle 440 (e.g., clockwise), the threaded portion 418 causes the reducing member 416 to move proximally in the direction of arrow B. For example, the threaded portion 418 is configured to rotatably connect and engage a corresponding internal helical thread (not shown) on an inner portion of the reducing member 416 to cause translation of the reducing member 416. After the vertebrae or element has been reduced, a torque may be applied in the opposite direct (e.g., counter-clockwise) the reducing member 416 is able to return to its original position such that the reducing member 416 moves distally in a direction opposite to arrow B.

Figure 13A:
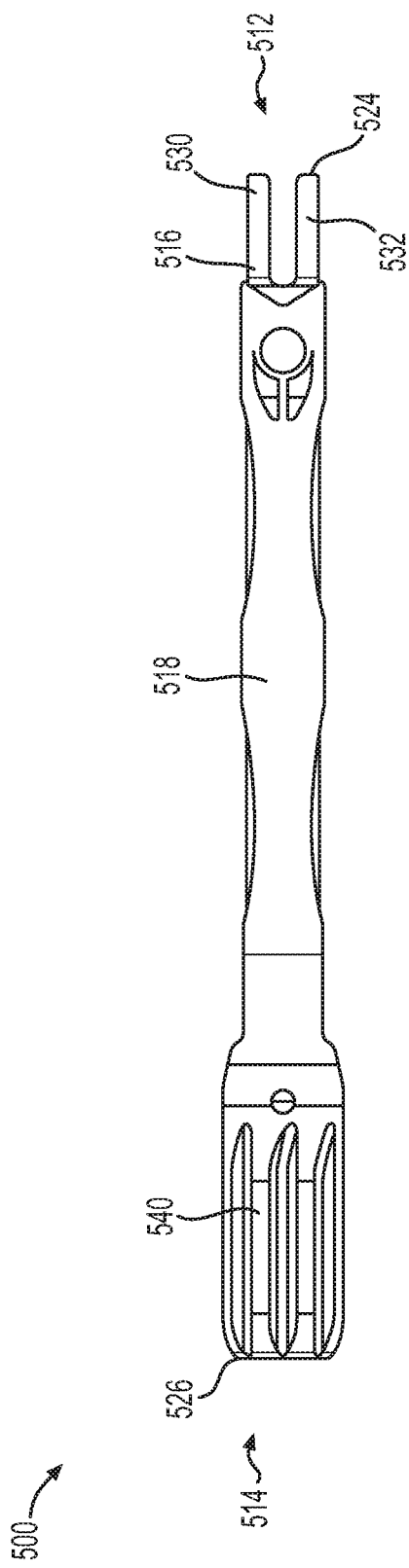
FIG. 13A depicts a side view and FIG. 13B provides a top view of an embodiment of an instrument with a reducer.
Figure 13B:
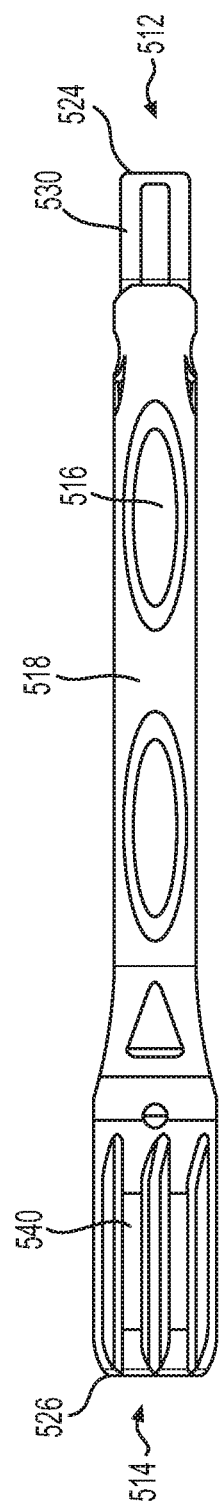

According to yet another embodiment, FIGS. 13A and B depicts a reducer 500. The reducer 500 includes a reducing member 516 having a generally cylindrical longitudinal body and outer longitudinal member 518. The reducing member 516 and has a working end 524 and a proximate end 526 extending from a distal end 512 toward a proximal end 514. The reducing member 516 is generally hollow and defines a channel extending longitudinally through it from the working end 524 to the proximate end 526.

The working end 524 of the reducing member 516 is adapted to receive a portion of a bone fastener including a tulip, yoke, or the like. In particular, the working end 524 is adapted to mate with an instrument or device, such as a fastener (e.g., a screw), a tulip, a rod, or the like. In this regard, the working end 524 may be forked and made up of a pair of opposing prongs 530, 532. The prongs 530, 532 each have an interior wall which defines one or more catches (not shown) that are adapted to mate with at least a portion of a pedicle screw assembly. These catches may include the spring tabs 204 and ramped surfaces 210 discussed above. For example, the catches may have a shape that complements or corresponds to the shape of the outer surface of a receiver element, fastener, tulip, yoke, or coupling element.

The outer longitudinal member 518 has a body which is generally hollow and defines a channel extending longitudinally through it and is sized and shaped to receive the reducing member 516 therein. The reducing member 516 may be able to translate or move, for example, in a proximal direction when a rotation force is applied to the handle 540. As a torque is applied to the handle 540 (e.g., clockwise), the reducing member 516 move proximally into the longitudinal member 518.

According to another embodiment, a kit may be provided including any of the surgical instruments in combination with the devices and implants described herein. The kits may include one or more devices, tools, materials, and the like that may be useful in conjunction with the instruments described. In particular, a kit may include a driver and one or more fasteners, such as bone screws. A kit may include an inserter with one or more fasteners (e.g., pedicle screws), tulips, rods, locking caps, for example, as described in U.S. Publication No. 2013/0018428. A kit may include a reducer with one or more fasteners (e.g., pedicle screws), tulips, rods, locking caps, etc. A kit may also include a combination of instruments including drivers, inserters, reducers, retractors, distractors, compressors, and the like, along with spinal implants, devices, fixation elements, etc.

The surgical instruments and devices disclosed herein can be formed of any suitable surgical material. Preferably, the surgical devices are comprised of one or more physiologically compatible or biocompatible materials, for example, that have the property or characteristic of not generating injury, toxicity, or immunological reaction to living tissues. Suitable physiologically compatible or biocompatible materials include, but are not limited to plastics, such as polyether ether ketone (PEEK), polyether ketone ketone (PEKK), or ultra-high molecular weight (UHMW) polyethylene; metals, such as surgical stainless steel, titanium, titanium alloys, surgical steel, metal alloys; and other materials known in the art. The surgical devices may also be made of a combination of suitable materials. In addition, the devices described herein may be sterilized by any suitable methods including, but not limited to, autoclaving, ethylene oxide, radiation, cold sterilization (e.g., hydrogen peroxide plasma), immersion sterilization, or a combination thereof.

The surgical device may serve a number of different functions, for example, including aiding insertion and securement of surgical devices and implements (e.g., implants, screws, and the like), improving performance of surgical procedures, and other similar functions. The devices are adapted to permit insertion through minimally invasive procedures, and are especially suitable for spinal surgeries and procedures. By way of example, the spinal surgeries may include, but are not limited to, insertion of vertebral fusion and fixation devices, including rods, plates, cables, bone anchors, fasteners, such as screws, and the like, or any surgical procedure.

Although the invention has been described in detail and with reference to specific embodiments, it will be apparent to one skilled in the art that various changes and modifications can be made without departing from the spirit and scope of the invention. Thus, it is intended that the invention covers the modifications and variations of this invention provided they come within the scope of the appended claims and their equivalents. It is expressly intended, for example, that all ranges broadly recited in this document include within their scope all narrower ranges which fall within the broader ranges. It is also intended that the components of the various devices disclosed above may be combined or modified in any suitable configuration.

What is claimed is:

1. A surgical instrument for inserting a surgical device comprising:
    a body having an outer housing and a handle, the outer housing having a longitudinal body with a channel extending therethrough and a distal tip configured to engage the surgical device;
    a shaft including a release shaft having a distal end configured to contact the surgical device and a second end, the shaft being housed within the channel of the outer housing, the shaft including a rack having a longitudinal body with a plurality of teeth;
    a pinion having a plurality of teeth radially extending therefrom and configured to mate with the plurality of teeth of the rack, and a cam having a generally circular body with at least one projection which is rotatably attached to the pinion and the body; and
    a trigger coupled to the handle and a linkage connecting the trigger to the second end of the shaft,
    wherein, when the trigger is initially depressed, the linkage moves the shaft and secures the surgical device to the distal tip.

2. The device of claim 1, wherein, when the trigger is fully depressed, the linkage moves the rack linearly, which rotates the pinion and the cam and thereby moves the release shaft distally and releases the surgical device.

3. The device of claim 1, wherein the release shaft comprises at least one tab which extends past the distal tip of the outer housing when the trigger is fully depressed.

4. The device of claim 1, wherein the trigger is connected to the second end of the shaft with a coupling element which is retained in a longitudinal opening in the handle to provide linear motion to the shaft.

5. The device of claim 1, wherein the distal tip includes at least two spring tabs configured to secure the surgical device.

6. The device of claim 5, wherein the spring tabs each have a ramped surface configured to allow an axial force to couple the surgical device and a ledge configured to retain at least a portion of the surgical device.

7. The device of claim 6, wherein the outer housing includes one or more spring cuts designed to allow the spring tabs to flex when the surgical device is secured or released.

8. The device of claim 1 further comprising a safety lock and a pin, the pin being receivable within an opening in the distal tip to lock the device.

9. The device of claim 8, wherein the safety lock defines a non-linear opening, the safety lock is coupled to the pin with a coupling element, and the coupling element is positioned within the non-linear opening to translate motion from the safety lock to the pin.

10. A method of using the instrument of claim 8 comprising:
    unlocking the instrument by depressing the safety lock;
    connecting the surgical device to the distal tip of the instrument by applying an axial force;
    locking the surgical device to the instrument by slightly depressing the trigger;
    performing a surgical procedure; and
    releasing the surgical device from the instrument by fully depressing the trigger.

11. The device of claim 1, wherein the surgical device is a screw, a tulip, a yoke, or a connector.

12. A kit comprising the instrument of claim 1 and a plurality of fixation devices including fasteners, tulips, and rods.

13. A surgical instrument for driving a fastening element, comprising:
    an outer housing and a shaft contained within the outer housing,
    a locking element connected to the shaft and having an engaging face with a first plurality of ratchet teeth, the locking element configured to move longitudinally along the shaft;
    the outer housing comprising a handle having a contacting face with a second plurality of ratchet teeth sized and dimensioned to correspond with the first plurality of ratchet teeth; and
    a locking button disposed on the locking element and configured to engage the shaft such that when the locking button is depressed, the first plurality of ratchet teeth on the engaging face are contacting the second plurality of ratchet teeth on the contacting face and a ratcheting mechanism is engaged.

14. The surgical instrument of claim 13, wherein the shaft further comprises a notch, and when the locking button is engaged in the notch, the first plurality of ratchet teeth on the engaging face are separated a distance from the second plurality of ratchet teeth on the contacting face and the ratcheting mechanism is not engaged.

15. The surgical instrument of claim 13, wherein the locking element further comprises a spring and the spring surrounds the shaft, and wherein the spring is configured to keep the ratcheting mechanism engaged.

* * * * *